United States Patent
Bannister et al.

(10) Patent No.: US 9,427,422 B2
(45) Date of Patent: *Aug. 30, 2016

(54) COMPOSITIONS FOR TREATING CARDIOVASCULAR DISEASES

(71) Applicant: Infirst Healthcare Limited, London (GB)

(72) Inventors: Robin Mark Bannister, Essex (GB); John Brew, Hertfordshire (GB); Suzanne Jane Dilly, Oxfordshire (GB); Gregory Alan Stoloff, London (GB); Wilson Caparros-Wanderley, Buckinghamshire (GB)

(73) Assignee: Infirst Healthcare Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/520,159

(22) Filed: Oct. 21, 2014

(65) Prior Publication Data

US 2015/0051235 A1   Feb. 19, 2015

Related U.S. Application Data

(63) Continuation of application No. 13/365,828, filed on Feb. 3, 2012, now Pat. No. 8,895,537, which is a continuation-in-part of application No. PCT/GB2011/052115, filed on Oct. 31, 2011.

(30) Foreign Application Priority Data

| Oct. 29, 2010 | (GB) | 1018289.7 |
|---|---|---|
| Feb. 4, 2011 | (GB) | 1101937.9 |
| Aug. 10, 2011 | (GB) | 1113728.8 |
| Aug. 10, 2011 | (GB) | 1113729.6 |
| Aug. 10, 2011 | (GB) | 1113730.4 |

(51) Int. Cl.

| A61K 31/55 | (2006.01) |
|---|---|
| A61K 31/47 | (2006.01) |
| A61K 31/40 | (2006.01) |
| A61K 31/19 | (2006.01) |
| A61K 31/192 | (2006.01) |
| A61K 9/08 | (2006.01) |
| A61K 47/44 | (2006.01) |
| A61K 9/20 | (2006.01) |
| A61K 31/60 | (2006.01) |
| A61K 47/10 | (2006.01) |
| A61K 47/14 | (2006.01) |
| A61K 47/34 | (2006.01) |
| A61K 31/215 | (2006.01) |
| A61K 31/22 | (2006.01) |
| A61K 31/216 | (2006.01) |

(52) U.S. Cl.
CPC ............ *A61K 31/192* (2013.01); *A61K 9/08* (2013.01); *A61K 9/2013* (2013.01); *A61K 31/60* (2013.01); *A61K 47/10* (2013.01); *A61K 47/14* (2013.01); *A61K 47/34* (2013.01); *A61K 47/44* (2013.01); *A61K 31/215* (2013.01); *A61K 31/216* (2013.01); *A61K 31/22* (2013.01); *A61K 31/40* (2013.01)

(58) Field of Classification Search
CPC ..... A61K 31/216; A61K 31/22; A61K 31/40
USPC ............... 514/217.12, 311, 419, 422, 568
See application file for complete search history.

(56) References Cited

U.S. PATENT DOCUMENTS

| 3,228,831 | A | 1/1966 | Nicholson et al. |
|---|---|---|---|
| 3,800,038 | A | 3/1974 | Rudel |
| 4,571,400 | A | 2/1986 | Arnold |
| 4,684,666 | A | 8/1987 | Haas |
| 4,918,103 | A | 4/1990 | Park et al. |
| 5,011,852 | A | 4/1991 | Park et al. |
| 5,059,626 | A | 10/1991 | Park et al. |
| 5,154,930 | A | 10/1992 | Popescu |
| 5,552,160 | A | 9/1996 | Liversidge et al. |
| 5,645,856 | A | 7/1997 | Lacy et al. |
| 5,955,451 | A | 9/1999 | Lichtenberger et al. |
| 6,267,985 | B1 | 7/2001 | Chen et al. |
| 6,294,192 | B1 | 9/2001 | Patel et al. |
| 6,319,513 | B1 | 11/2001 | Dobrozsi |
| 6,383,471 | B1 | 5/2002 | Chen et al. |
| 6,451,339 | B2 | 9/2002 | Patel et al. |
| 6,923,988 | B2 | 8/2005 | Patel et al. |
| 7,473,432 | B2 | 1/2009 | Cevc et al. |
| 2003/0008003 | A1 | 1/2003 | Jamali |

(Continued)

FOREIGN PATENT DOCUMENTS

| CN | 1736369 | 2/2006 |
|---|---|---|
| CN | 101129335 A | 2/2008 |

(Continued)

OTHER PUBLICATIONS

Vane JR et al., Mechanism of action of anti-inflammatory drugs, Int J Tissue React. 1998;20(1):3-15, abstract.

(Continued)

*Primary Examiner* — Kevin E Weddington

(74) *Attorney, Agent, or Firm* — One3 IP Management, P.C.; Dean G. Stathakis; Peter D. Weinstein

(57) ABSTRACT

The present specification discloses pharmaceutical compositions, methods of preparing such pharmaceutical compositions, and methods and uses of treating a cardiovascular disease in an individual using such pharmaceutical compositions.

20 Claims, 3 Drawing Sheets

(56) References Cited

U.S. PATENT DOCUMENTS

| | | |
|---|---|---|
| 2003/0170279 A1 | 9/2003 | Lambert et al. |
| 2003/0232097 A1 | 12/2003 | Radhakrishnan et al. |
| 2004/0024057 A1 | 2/2004 | Earl et al. |
| 2004/0253276 A1 | 12/2004 | Sato et al. |
| 2005/0152968 A1 | 7/2005 | Brophy et al. |
| 2006/0062810 A1 | 3/2006 | Woo et al. |
| 2006/0078616 A1 | 4/2006 | Georgewill et al. |
| 2007/0015834 A1 | 1/2007 | Flashner-Barak et al. |
| 2007/0036831 A1 | 2/2007 | Baker |
| 2007/0104741 A1 | 5/2007 | Murty et al. |
| 2007/0190080 A1 | 8/2007 | Friedman |
| 2007/0203173 A1 | 8/2007 | Mudumba et al. |
| 2008/0153894 A1 | 6/2008 | Britten et al. |
| 2008/0154210 A1 | 6/2008 | Jordan et al. |
| 2009/0304782 A1 | 12/2009 | De Blas et al. |
| 2010/0099767 A1 | 4/2010 | Davis |
| 2010/0125060 A1 | 5/2010 | Razzak et al. |
| 2011/0142945 A1 | 6/2011 | Chen et al. |
| 2011/0195993 A1 | 8/2011 | Masson et al. |
| 2012/0270845 A1 | 10/2012 | Bannister et al. |
| 2012/0270899 A1 | 10/2012 | Bannister et al. |
| 2013/0156853 A1 | 6/2013 | Zhang |

FOREIGN PATENT DOCUMENTS

| | | | | |
|---|---|---|---|---|
| CN | 102793628 A | 11/2012 | | |
| EP | 306060 A2 | 3/1989 | | |
| EP | 0521344 A2 | 1/1993 | | |
| GB | 2331458 A | 5/1999 | | |
| GB | 2477590 A | 8/2011 | | |
| JP | 6009381 | 3/1992 | | |
| JP | 2008143807 | 12/2006 | | |
| JP | 2009155282 | 7/2009 | | |
| NL | EP 1923060 A1 * | 5/2008 | ........... | A61K 31/133 |
| WO | 92/09272 A1 | 6/1992 | | |
| WO | 95/11039 A1 | 4/1995 | | |
| WO | 9703655 A1 | 2/1997 | | |
| WO | 98/25595 A1 | 6/1998 | | |
| WO | 00/27372 A1 | 5/2000 | | |
| WO | 0057859 A1 | 5/2000 | | |
| WO | 00/67728 A2 | 11/2000 | | |
| WO | 00/76478 A1 | 12/2000 | | |
| WO | 02/085414 A2 | 10/2002 | | |
| WO | 03/013566 A1 | 2/2003 | | |
| WO | 2004/082588 A2 | 9/2004 | | |
| WO | 2005/009436 A1 | 2/2005 | | |
| WO | 2006/099325 A2 | 9/2006 | | |
| WO | 2008/070950 A1 | 6/2008 | | |
| WO | 2008/120207 A3 | 10/2008 | | |
| WO | 2008/134512 A1 | 11/2008 | | |
| WO | 2009/033131 A2 | 3/2009 | | |
| WO | 2009/047785 A3 | 4/2009 | | |
| WO | 2009/067734 A1 | 6/2009 | | |
| WO | 2009/069717 A1 | 6/2009 | | |
| WO | 2010/059717 A2 | 5/2010 | | |
| WO | 2010/087947 A2 | 8/2010 | | |
| WO | 2010/097332 A1 | 9/2010 | | |
| WO | 2010/097334 A1 | 9/2010 | | |
| WO | 2010103312 A1 | 9/2010 | | |
| WO | 2011/095814 A1 | 8/2011 | | |
| WO | 2012/056251 A1 | 5/2012 | | |
| WO | 2012/104654 A1 | 8/2012 | | |
| WO | 2012/104655 A2 | 8/2012 | | |

OTHER PUBLICATIONS

Csizmazia, E., et al., Penetration enhancer effect of sucrose laurate and Transcutol on ibuprofen, Journal of Drug Delivery Science and Technology, vol. 21, No. 5 Sep. 2011 XP009168551.

Hesson Chung, et al., Oil Components Modulate Physical Characteristics and Function of the Natural Oil Emulsions as Drug or Gene Delivery System, Journal of Controlled Release 71:339-350 (2001).

List et al., Hydrogenation of Soybean Oil Triglycerides: Effect of Pressure on Selectivity. JAOCS (2000), vol. 77, pp. 311-314.

Nickitas-Etienne, PCT International Preliminary Report on Patentability, PCT/GB2011/050189, pp. 11 (Aug. 7, 2012).

Nickitas-Etienne, PCT International Preliminary Report on Patentability, PCT/GB2011/052115, pp. 8 (Apr. 30, 2013).

PCT International Search Report and The Written Opinion of the Internation Searching Authority PCT/EP2014/050627.

PCT International Search Report and The Written Opinion of the Internation Searching Authority PCT/EP2014/050628.

PCT International Search Report and The Written Opinion of the Internation Searching Authority PCT/EP2014/050637.

Schule, PCT International Search Report & Written Opinion, PCTGB2012050241, pp. 24 (Jul. 13, 2012).

Schule, PCT International Search Report & Written Opinion, PCTGB2012050242, pp. 12 (Jan. 22, 2013).

Strickley, Solubilizing Excipients in Oral and Inkectable Formulations Pharaceutical (2004), vol. 21, pp. 21, pp. 201-230.

Wolfgang Grebe, et al., A Multicenter, Randomized, Double-Blind, Double-Dummy, Placebo- and Active-Controlled, Parallel-Group Comparison of Diclofenac-K and Ibuprofen for the Treatment of Adults with Influenza-like Symptoms, Clinical Therapeutics 25(2): 444-459 (2003).

* cited by examiner

COMPOSITIONS FOR TREATING CARDIOVASCULAR DISEASES

This continuation application claims priority pursuant to 35 U.S.C. §120 to U.S. patent application Ser. No. 13/365,828, filed Feb. 3, 2012, a continuation-in-part application that claims priority to patent application PCT/GB2011/052115, filed Oct. 31, 2011, an international patent application that claims priority to GB 1018289.7, filed Oct. 29, 2010, and claims priority to GB 1113730.4, filed Aug. 10, 2011, GB 1113729.6, filed Aug. 10, 2011, GB 1113728.8, filed Aug. 10, 2011, and GB 1101937.9, filed Feb. 4, 2011, each of which is hereby incorporated by reference in its entirety.

Lipids constitute a broad group of naturally occurring hydrophobic or amphiphilic molecules that include fatty acids, glycerolipids, glycerophospholipids, sphingolipids, saccharolipids, and polyketides, sterol lipids and prenol lipids. The main biological functions of lipids include energy storage, as structural components of cell membranes, and as important signaling molecules. Given these fundamental roles, all cells use and rely on lipids. One process used to transport lipids to cells involves apolipoproteins. Apolipoproteins are proteins that bind to lipids to form lipoproteins, which are the vehicles used for transporting the lipids, including triglycerides and cholesterol, through the lymphatic and circulatory systems. The lipid components of lipoproteins are not themselves soluble in water. However, because of their amphipathic properties, apolipoproteins and other amphipathic molecules (such as, e.g., phospholipids) can surround the lipids, creating the lipoprotein particle that is itself water-soluble, and can thus be carried through water-based circulation, i.e. blood and lymph, etc.

There five major groups of lipoprotein particles, and the lipoprotein density and type of apolipoproteins it contains determines the fate of the particle and its influence on metabolism. Chylomicrons are the largest lipoprotein particle and these particles carry triglycerides from the intestines to the liver, skeletal muscle, and adipose tissue. Very low-density lipoprotein (VLDL) particles are large, triglyceride-rich lipoprotein secreted by the liver that transports triglycerides to adipose tissue and muscle. The third group lipoprotein particles are intermediate-density lipoprotein (IDL) particles, an intermediate between VLDL and low-density lipoprotein (LDL). IDL particles are formed when lipoprotein lipase removes triglycerides from VLDL particles in the capillaries and the return these smaller particles to the circulation. The IDL particles have lost most of their triglyceride, but they retain cholesteryl esters. Some of the IDL particles are rapidly taken up by the liver; others remain in circulation, where they undergo further triglyceride hydrolysis and are converted to LDL. LDL particles carry cholesterol from the liver to cells of the body, where these particles bind to LDL receptors that are subsequently endocytosed in vesicles form via clathrin-coated pits. After the clathrin coat is shed, the vesicles ultimately deliver the LDL to lysosomes where the cholesterol esters are hydrolyzed. The last group of lipoprotein particles is high-density lipoprotein (HDL) particles, which collect cholesterol from the body's tissues and bring it back to the liver.

High levels of lipids, e.g., cholesterol, and/or lipoprotein particles, e.g., VLDL, IDL, and/or LDL can have deleterious effects on the cardiovascular system. For example, as a major extracellular carrier of cholesterol, LDL plays important physiologic roles in cellular function and regulation of metabolic pathways. Cells have complex feedback mechanisms that ensure sufficient supply of cholesterol and prevent its excessive accumulation in the blood. However, under pathologic conditions of, e.g., hyperlipidemia, oxidative stress and/or genetic disorders, specific components of LDL become oxidized or otherwise modified, with a consequence that cholesterol transport by such modified LDL is diverted from its physiologic targets and accumulates in the blood.

One effect of this accumulation is the high amounts of cholesterol and/or LDL become embedded in the walls of blood vessels, an in so doing invokes an inflammatory response. In response to this inflammation, blood monocytes adhere to the endothelium, transmigrate into the subendothelial space, and differentiate toward macrophages. Macrophages, in turn, engulf the cholesterol deposits and modified LDL by phagoocytosis via scavenger receptors, which are distinct from LDL receptors. However, the adaptive mechanisms mediated by macrophages are not sufficient to process the uncontrolled cholesterol and/or LDL deposition seen under pathologic conditions. As a result, the lipid-laden macrophages transform into "foam cells" or "foamy cells" having a M1 phenotype. Both cholesterol/LDL deposition and the attendant foam cell-mediated pro-inflammatory reactions in the blood wall lead to the development of atherosclerotic lesions. Left untreated, this lipid accumulation and pro-inflammatory response result in the progression of the lesions, which eventually leads to a cardiovascular disease.

Another effect of high cholesterol/LDL accumulation in the blood is the formation LDL aggregates or LDL agglomerates. Being of high molecular weight, LDL agglomerates initiate an inflammatory response in a manner similar to that invoked by pathogens like viruses or bacteria. The inflammatory response triggers agglomerate uptake by macrophages which converts these cells into foam cells having a M1 phenotype, and the release of inflammation inducing molecules. Once again, left untreated, the lipid accumulation and pro-inflammatory response can result in a cardiovascular disease.

Attempts to treat cardiovascular disease by controlling levels of lipids and/or lipoproteins in the blood have met with limited success. For example, although administration of statins reduces cardiovascular risk in some individuals, these therapeutic compounds do not reduce triglyceride levels. Thus, in individuals at cardiovascular risk who exhibit deleteriously high levels of triglycerides, another class of therapeutic compounds called fibrates may be administered. However, although lowering triglyceride and LDL levels, fibrates do not affect the level of HDL, the lipoprotein particle known to be protective against cardiovascular disease. Lastly, combination treatments involving statins and fibrates, while effective, cause a significant increase to the risk of myopathy and rhabdomyolysis, and therefore can only be carried out under very close medical supervision. In view of these problems, there is, therefore, clearly a need for improved compounds and compositions for the use and treatment of cardiovascular diseases, including those associated with high lipid and/or lipoprotein levels.

The present specification discloses pharmaceutical compositions and methods for treating an individual suffering from a cardiovascular disease. The pharmaceutical compositions disclosed herein are essentially a lipid delivery system that enables a therapeutic compound having an activity that modulates lipid and/or lipoprotein levels to be delivered in a manner that more effectively treats a cardiovascular disease.

SUMMARY

Aspects of the present specification disclose a pharmaceutical composition comprising a therapeutic compound and a pharmaceutically-acceptable adjuvant. A therapeutic compound may have an activity that normalizes lipid levels. Other aspects of the present specification disclose a pharmaceutical composition comprising a therapeutic compound disclosed herein, a pharmaceutically-acceptable solvent, and a pharmaceutically-acceptable adjuvant. In other aspects, the pharmaceutical compositions disclosed herein further comprise a pharmaceutically-acceptable stabilizing agent.

Other aspects of the present specification disclose a method of preparing a pharmaceutical composition, the method comprising the step of contacting a therapeutic compound with a pharmaceutically-acceptable adjuvant under conditions which allow the formation of the pharmaceutical composition. Other aspects of the present specification disclose a method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has an activity that normalizes lipid levels, and b) contacting the solution formed in step (a) with a pharmaceutically-acceptable adjuvant under conditions which allow the formation of the pharmaceutical composition. In other aspects, the method of preparing disclosed herein further comprises c) removing the pharmaceutically-acceptable solvent from the pharmaceutical composition.

Other aspects of the present specification disclose a pharmaceutical composition, the pharmaceutical composition made according to a method comprising the step of contacting a therapeutic compound with a pharmaceutically-acceptable adjuvant under conditions which allow the formation of the pharmaceutical composition. Other aspects of the present specification disclose a pharmaceutical composition, the pharmaceutical composition made according to a method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has an activity that normalizes lipid levels, and b) contacting the solution formed in step (a) with a pharmaceutically-acceptable adjuvant under conditions which allow the formation of the pharmaceutical composition. In other aspects, the method of making a pharmaceutical composition disclosed herein further comprises c) removing the pharmaceutically-acceptable solvent from the pharmaceutical composition.

Other aspects of the present specification disclose a method of treating an individual with a cardiovascular disease, the method comprising the step of administering to the individual in need thereof a pharmaceutical composition disclosed herein, wherein administration results in a reduction in a symptom associated with the cardiovascular disease, thereby treating the individual.

Other aspects of the present specification disclose a use of a pharmaceutical composition disclosed herein in the manufacture of a medicament for the treatment of a cardiovascular disease.

Other aspects of the present specification disclose a use of a pharmaceutical composition disclosed herein for the treatment of a cardiovascular disease.

BRIEF DESCRIPTION OF THE DRAWINGS

FIG. 2A shows a graph of the effects of a pharmaceutical composition disclosed herein on in vivo levels of IL-10, whereas FIG. 2B shows a graph of the effects of a pharmaceutical composition disclosed herein on in vivo levels of IL-4. BC1054 ORAL=Group A; Vehicle ORAL=Group B; and BC1054 Lipid ORAL=Group C.

FIG. 3A shows a graph of the effects of a pharmaceutical composition disclosed herein on in vivo levels of IL-10; FIG. 3B shows a graph of the effects of a pharmaceutical composition disclosed herein on in vivo levels of TNF-α; and FIG. 3C shows a graph of the effects of a pharmaceutical composition disclosed herein on in vivo levels of IFN-γ. BC1054 ORAL=Group A; Vehicle ORAL=Group B; and BC1054 Lipid ORAL=Group C.

DESCRIPTION

Figure 1:
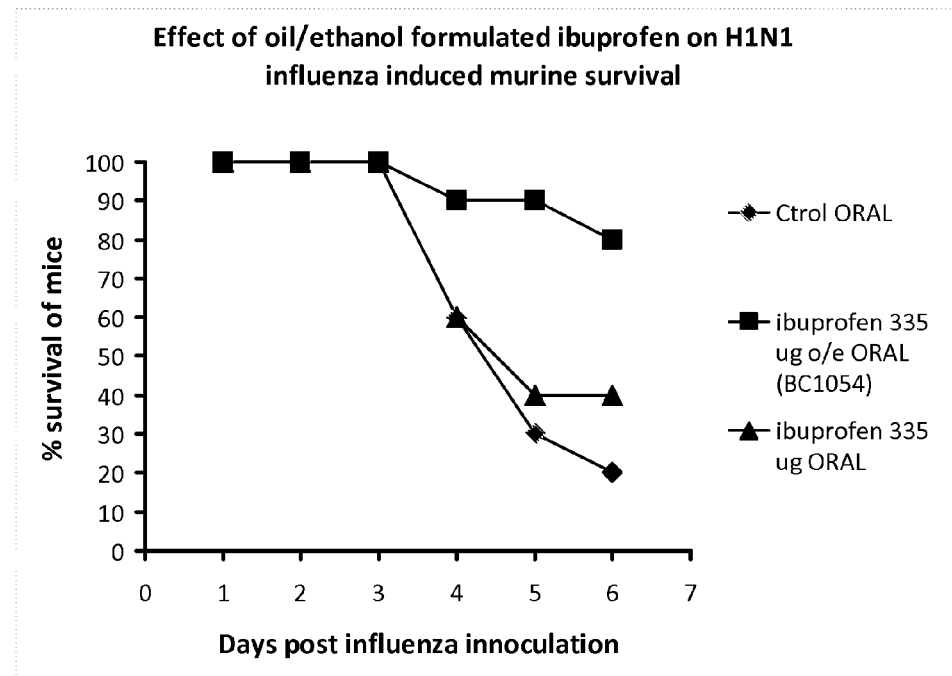
FIG. 1 shows the effects of a pharmaceutical composition disclosed herein on survival against Influenza A/PR/8/34 lethal challenge. Ibuprofen 335 μg=Group A; Ctrol ORAL=Group B; and ibuprofen 335 μg o/e ORAL (BC1054)=Group C.

Aspects of the present specification disclose, in part, a pharmaceutical composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In one embodiment, a pharmaceutical composition disclosed herein comprises a therapeutic compound having an activity that normalizes lipid levels and a pharmaceutically-acceptable adjuvant. In another embodiment, a pharmaceutical composition disclosed herein comprises a therapeutic compound having an activity that normalizes lipid levels, a pharmaceutically-acceptable solvent, and a pharmaceutically-acceptable adjuvant. In aspects of this embodiment, a pharmaceutical composition disclosed herein may further comprise a pharmaceutically-acceptable stabilizing agent. In other aspects of this embodiment, a pharmaceutical composition disclosed herein may further comprise a pharmaceutically-acceptable carrier, a pharmaceutically-acceptable component, or both pharmaceutically-acceptable carrier and pharmaceutically-acceptable component.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may have an activity that normalizes lipid levels. As used herein, the term "normalizes lipid levels" refers to an activity that reduces a level of a lipid or lipoprotein that is deleteriously high to a normal or non-harmful level, increases a level of a lipid or lipoprotein to a level that is beneficial to an individual, or both. For example, a therapeutic compound having an activity that normalizes lipid levels may reduce cholesterol and/or LDL that is deleteriously high to a normal or non-harmful level, increase HDL to a level that is beneficial to an individual, or both.

Lipid and lipoprotein abnormalities are common in the general population, and are regarded as a modifiable risk factor for cardiovascular disease due to their influence on atherosclerosis. Because studies have shown that higher levels of LDL particles promote health problems and cardiovascular disease, they are often informally called the "bad cholesterol" particles. This is in contrast to HDL particles, which are frequently referred to as "good cholesterol" or "healthy cholesterol" particles, because higher HDL levels are correlated with cardiovascular health. High levels of HDL are thought to reduce LDL levels by acting as a sink for excess triglycerides levels in LDL.

In an embodiment, a therapeutic compound disclosed herein has an anti-hyperlipidemia activity. In an aspect of this embodiment, a therapeutic compound disclosed herein has anti-hyperlipidemia activity capable of reducing the levels of VLDL, IDL, LDL, or a combination thereof. In other aspects of this embodiment, a therapeutic compound disclosed herein has anti-hyperlipidemia activity capable of reducing the levels of VLDL, IDL, LDL, or a combination thereof by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has anti-hyperlipidemia activity capable of reducing the levels of VLDL, IDL, LDL, or a combination thereof in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein increases the level of HDL. In an aspect of this embodiment, a therapeutic compound disclosed herein increases the level of HDL by, e.g., at least 2%, at least 3%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45% or at least 47%. In yet other aspects of this embodiment, a therapeutic compound disclosed herein increases the level of HDL in a range from, e.g., about 2% to about 100%, about 10% to about 50%, about 15% to about 50%, about 20% to about 50%, about 25% to about 50%, about 30% to about 50%, about 35% to about 50%, about 40% to about 50%, about 2% to about 45%, about 10% to about 45%, about 15% to about 45%, about 20% to about 45%, about 25% to about 45%, about 30% to about 45%, about 35% to about 45%, about 2% to about 40%, about 10% to about 40%, about 15% to about 40%, about 20% to about 40%, about 25% to about 40%, or about 30% to about 40%, about 2% to about 35%, about 10% to about 35%, about 15% to about 35%, about 20% to about 35%, or about 25% to about 35%.

When cholesterol and/or lipoproteins like LDL become embedded in the walls of blood vessels, an immune response can be invoked that subsequently results in a chronic inflammatory response. Such chronic inflammation can that eventually can weaken and damage the blood vessels, causing them to burst. Thus, one consequence of modulating the levels of a lipid or lipoprotein is the reduction or elimination of a chronic inflammation. Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxidase proliferator-activator receptor gamma (PPAR-γ) signaling. PPARγ signaling pathway 1) induces apoptosis of Macrophage M1 cells, thereby reducing the levels of Th1 pro-inflammatory cytokines and 2) promotes differentiation of monocytes into Macrophage M2 cells. Macrophage M2 cells produce and release Th2 anti-inflammatory cytokines.

In an embodiment, a therapeutic compound disclosed herein has an anti-inflammatory activity capable of reducing the levels of an inflammation inducing prostaglandin. In other aspects of this embodiment, a therapeutic compound disclosed herein has an anti-inflammatory activity capable of reducing the levels of a inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of a inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein has an anti-inflammatory activity substantially similar to 15dPGJ2. In aspects of this embodiment, a therapeutic compound disclosed herein an anti-inflammatory activity that is, e.g., at least 5%, at least 15%, at least 25%, at least 50%, at least 55%, at least 60%, at least 65%, at least 70%, at least 75%, at least 80%, at least 85%, at least 90% or at least 95% of the activity observed for 15dPGJ2. In other aspects of this embodiment, a therapeutic compound disclosed herein an anti-inflammatory activity that is in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50% of the activity observed for 15dPGJ2.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGJ2 (a prostaglandin), whereas PPAR-α is activated by leukotriene B4.

The de novo production of HDL particles by the liver is thought to be triggered by activation of the PPAR signaling pathways. So PPAR agonists that are targeted to cell types involved in lipid processing (macrophage, adipocytes and hepatocytes) through the normal lipid absorption mechanism will selectively increase beneficial HDL levels and so normalize blood lipid profiles and treat a cardiovascular disease.

In an embodiment, a therapeutic compound disclosed herein has an anti-inflammatory activity capable of stimulating all PPAR signaling pathways. Such a therapeutic compound includes a PPAR pan-agonist. In other embodiments, a therapeutic compound disclosed herein has an anti-inflammatory activity capable of stimulating one or two of the PPAR signaling pathways. Such a therapeutic compound includes a selective PPAR agonist.

In another embodiment, a therapeutic compound disclosed herein has an anti-inflammatory activity capable of stimulating a PPAR-α signaling pathway. In aspects of this embodiment, a therapeutic compound disclosed herein stimulates a PPAR-α signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-α signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPAR-δ signaling pathway. In aspects of this embodiment, a therapeutic compound disclosed herein stimulates a PPAR-δ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-δ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPARγ signaling pathway. A therapeutic compounds disclosed herein may be capable of binding to all isoforms of PPAR-γ, or may be capable of selectively binding to either PPAR-γ1, PPAR-γ2, PPAR-γ3, or any combination of two thereof. In aspects of this embodiment, a therapeutic compound disclosed herein stimulates a PPARγ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPARγ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

Macrophages are activated and polarized into distinct phenotypes expressing unique cell surface molecules and secreting discrete sets of cytokines and chemokines. The classical M1 phenotype supports pro-inflammatory Th1 responses driven by cytokines such as, e.g., Interleukin-6 (IL-6), IL-12 and IL-23, while the alternate M2 phenotype is generally supportive of anti-inflammatory processes driven by IL-10. M2 cells can be further classified into subsets, M2a, M2b, and M2c, based on the type of stimulation and the subsequent expression of surface molecules and cytokines.

In yet another embodiment, a therapeutic compound disclosed herein has an anti-inflammatory activity capable of promoting the resolving phenotypic change of M1 to M2. In an aspect of this embodiment, a therapeutic compound disclosed herein has an anti-inflammatory activity capable of inducing apoptosis of Macrophage M1 cells. In another aspect of this embodiment, a therapeutic compound disclosed herein has an anti-inflammatory activity capable of promoting differentiation of Macrophage M2 cells. In yet another aspect of this embodiment, a therapeutic compound disclosed herein has an anti-inflammatory activity capable of inducing apoptosis of Macrophage M1 cells and promoting differentiation of Macrophage M2 cells.

In still another embodiment, a therapeutic compound disclosed herein has an anti-inflammatory activity capable of modulating Th1 and Th2 cytokines. In an aspect of this embodiment, a therapeutic compound disclosed herein has an anti-inflammatory activity capable of reducing the levels of Interferon-gamma (IFNγ), Tumor necrosis factor-alpha (TNF-α), IL-12, or a combination thereof released from a Th1 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of increasing the levels of IL-10 released from a Th2 cell. In other aspects of this embodiment, a therapeutic compound disclosed herein has an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of increasing the levels of IL-10 released from a Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of reducing the levels of IFNγ, TNF-α, IL-12, or a combination thereof released from a Th1 cell and increasing the levels of IL-10 released from a Th2 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, and capable of increasing the levels of IL-10 released from a Th2 cell in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein has an anti-inflammatory activity capable of reducing the levels of an inflammation inducing molecule. In an aspect of this embodiment, a therapeutic compound disclosed herein has an anti-inflammatory activity capable of reducing the levels of substance P (SP), calcitonin gene-related peptide (CGRP), glutamate, or a combination thereof. In other aspects of this embodiment, a therapeutic compound disclosed herein has an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of SP, CGRP, glutamate, or a combination thereof released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may have a log P value indicating that the compound is soluble in an organic solvent. As used herein, the term "log value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound disclosed herein may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 nm$^2$, less than 7.0 nm$^2$, less than 6.0 nm$^2$, less than 5.0 nm$^2$, less than 4.0 nm$^2$, or less than 3.0 nm$^2$. In other aspects of this embodiment, a therapeutic compound disclosed herein may have a polar surface area in the range of, e.g., between 3.0 nm$^2$ and 6.5 nm$^2$, between 3.0 nm$^2$ and 6.0 nm$^2$, between 3.0 nm$^2$ and 5.5 nm$^2$, between 3.0 nm$^2$ and 5.0 nm$^2$, between 3.0 nm$^2$ and 4.5 nm$^2$, between 3.5 nm$^2$ and 6.5 nm$^2$, between 3.5 nm$^2$ and 6.0 nm$^2$, between 3.5 nm$^2$ and 5.5 nm$^2$, between 3.5 nm$^2$ and 5.0 nm$^2$, between 3.5 nm$^2$ and 4.5 nm$^2$, between 4.0 nm$^2$ and 6.5 nm$^2$, between 4.0 nm$^2$ and 6.0 nm$^2$, between 4.0 nm$^2$ and 5.5 nm$^2$, or between 4.0 nm$^2$ and 5.0 nm$^2$, between 4.0 nm$^2$ and 4.5 nm$^2$, or between 4.5 nm$^2$ and 5.5 nm$^2$. In yet other aspects of this embodiment, a therapeutic compound disclosed herein may have a polar surface area in the range of, e.g., between 2.0 nm$^2$ and 6.5 nm$^2$, between 2.0 nm$^2$ and 6.0 nm$^2$, between 2.0 nm$^2$ and 5.5 nm$^2$, between 2.0 nm$^2$ and 5.0 nm$^2$, between 2.0 nm$^2$ and 4.5 nm$^2$, between 2.5 nm$^2$ and 6.5 nm$^2$, between 2.5 nm$^2$ and 6.0 nm$^2$, between 2.5 nm$^2$ and 5.5 nm$^2$, between 2.5 nm$^2$ and 5.0 nm$^2$, or between 2.5 nm$^2$ and 4.5 nm$^2$.

A therapeutic compound disclosed herein may be a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, Aceclofenac, Acemetacin, Actarit, Alcofenac, Alminoprofen, Amfenac, Aloxipirin, Aminophenazone, Antraphenine, Aspirin, Azapropazone, Benorilate, Benoxaprofen, Benzydamine, Butibufen, Celecoxib, Chlorthenoxacin, Choline Salicylate, Clometacin, Dexketoprofen, Diclofenac, Diflunisal, Emorfazone, Epirizole; Etodolac, Etoricoxib, Feclobuzone, Felbinac, Fenbufen, Fenclofenac, Flurbiprofen, Glafenine, Hydroxyethyl salicylate, Ibuprofen, Indometacin, Indoprofen, Ketoprofen, Ketorolac, Lactyl phenetidin, Loxoprofen, Lumiracoxib, Mefenamic acid, Meloxicam, Metamizole, Metiazinic acid, Mofebutazone, Mofezolac, Nabumetone, Naproxen, Nifenazone, Niflumic acid, Oxametacin, Phenacetin, Pipebuzone, Pranoprofen, Propyphenazone, Proquazone, Protizinic acid, Rofecoxib, Salicylamide, Salsalate, Sulindac, Suprofen, Tiaramide, Tinoridine, Tolfenamic acid, Valdecoxib, and Zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, and a selective cyclooxygenase 2 (COX 2) inhibitor. A NSAID may be a profen. Examples of a suitable salicylate derivative NSAID include, without limitation, Acetylsalicylic acid (asprin), Diflunisal, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, and Suprofen. Examples of a suitable acetic acid derivative NSAID include, without limitation, Aceclofenac, Acemetacin, Actarit, Alcofenac, Amfenac, Clometacin, Diclofenac, Etodolac, Felbinac, Fenclofenac, Indometacin, Ketorolac, Metiazinic acid, Mofezolac, Nabumetone, Naproxen, Oxametacin, Sulindac, and Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitors include, without limitation, Celecoxib, Etoricoxib, Firocoxib, Lumiracoxib, Meloxicam, Parecoxib, Rofecoxib, and Valdecoxib.

A therapeutic compound disclosed herein may be a PPARγ agonist. Examples of a suitable PPARγ agonist include, without limitation, Benzbromarone, a cannabidiol, Cilostazol, Curcumin, Delta(9)-tetrahydrocannabinol, glycyrrhetinic acid, Indomethacin, Irbesartan, Monascin, mycophenolic acid, Resveratrol, 6-shogaol, Telmisartan, a thiazolidinedione like Rosiglitazone, Pioglitazone, and Troglitazone, a NSAID, and a fibrate. Other suitable PPARγ agonists are described in Masson and Caumont-Bertrand, *PPAR Agonist Compounds, Preparation and Uses*, US 2011/0195993, which is hereby incorporated by reference in its entirety.

A therapeutic compound disclosed herein may be a nuclear receptor binding agent. Examples of a suitable nuclear receptor binding agent include, without limitation, a Retinoic Acid Receptor (RAR) binding agent, a Retinoid X Receptor (RXR) binding agent, a Liver X Receptor (LXR) binding agent and a Vitamin D binding agent.

A therapeutic compound disclosed herein may be an anti-hyperlipidemic agent. There are several classes of anti-hyperlipidemic agents (also known as hypolipidemic agents). They may differ in both their impact on the cholesterol profile and adverse effects. For example, some may lower LDL, while others may preferentially increase HDL. Clinically, the choice of an agent will depend on the cholesterol profile of an individual, cardiovascular risk of an individual, and/or the liver and kidney functions of an individual. Examples of a suitable anti-hyperlipidemic agent include, without limitation, a fibrate, a statin, a tocotrienol, a niacin, a bile acid sequestrants (resin), a cholesterol absorption inhibitor, a pancreatic lipase inhibitor, and a sympathomimetic amine.

A therapeutic compound disclosed herein may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, Bezafibrate, Ciprofibrate, Clofibrate, Gemfibrozil, and Fenofibrate.

A therapeutic compound disclosed herein may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, Atorvastatin, Fluvastatin, Lovastatin, Pitavastatin, Pravastatin, Rosuvastatin, and Simvastatin.

A therapeutic compound disclosed herein may be a tocotrienol. Tocotrienols are another class of HMG-CoA reductase inhibitors and may be used to lower LDL and/or cholesterol levels by inducing hepatic LDL receptor upregulation and/or decreasing plasma LDL levels. Examples of a suitable tocotrienol include, without limitation, a γ-tocotrienol and a δ-tocotrienol.

A therapeutic compound disclosed herein may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of VLDL and cholesterol by the liver. By lowering VLDL levels, a niacin may also increase the level of HDL in blood. Examples of a suitable niacin include, without limitation, acipimox, niacin, nicotinamide, and vitamin B3.

A therapeutic compound disclosed herein may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, Cholestyramine, Colesevelam, and Colestipol.

A therapeutic compound disclosed herein may be a cholesterol absorption inhibitor. Cholesterol absorption inhibitors are a class of therapeutic compounds that inhibits the absorption of cholesterol from the intestine. Decreased cholesterol absorption leads to an upregulation of LDL-receptors on the surface of cells and an increased LDL-cholesterol uptake into these cells, thus decreasing levels of LDL in the blood plasma. Examples of a suitable cholesterol absorption inhibitor include, without limitation, Ezetimibe, a phytosterol, a sterol and a stanol.

A therapeutic compound disclosed herein may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, Orlistat.

A therapeutic compound disclosed herein may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine.

A therapeutic compound disclosed herein may be an ester of a therapeutic compound. An ester of a therapeutic compound increases the log P value relative to the same therapeutic compound, but without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively normalizes lipid levels and/or inhibits a pro-inflammatory response as long as the compound is combined with an adjuvant disclosed herein. In one embodiment, a therapeutic compound may be reacted with ethyl ester in order to form an ethyl ester of the therapeutic compound.

In another embodiment, a pharmaceutical composition disclosed herein does not comprise a pharmaceutically-acceptable solvent disclosed herein. In an aspect of this embodiment, a pharmaceutical composition comprises a therapeutic compound and a pharmaceutically-acceptable adjuvant, but does not comprise a pharmaceutically-acceptable solvent disclosed herein.

A pharmaceutical composition disclosed herein may comprise a therapeutic compound in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

Aspects of the present specification disclose, in part, a pharmaceutically-acceptable solvent. A solvent is a liquid, solid, or gas that dissolves another solid, liquid, or gaseous (the solute), resulting in a solution. Solvents useful in the pharmaceutical compositions disclosed herein include, without limitation, a pharmaceutically-acceptable polar aprotic solvent, a pharmaceutically-acceptable polar protic solvent and a pharmaceutically-acceptable non-polar solvent. A pharmaceutically-acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically-acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically-acceptable non-polar solvent includes, without limitation, pentane, cyclopentane, hexane, cyclohexane, benzene, toluene, 1,4-Dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically-acceptable alcohol. As used herein, the term "alcohol" refers to an organic molecule comprising a hydroxyl functional group (—OH) bond to a carbon atom, where the carbon atom is saturated. In aspects of this embodiment, the alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexyl and 2-(2-propyl)-5-methyl-cyclohexane-1-ol.

In another embodiment, a solvent may comprise an ester of pharmaceutically-acceptable alcohol and an acid. Suitable pharmaceutically-acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically-acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically-acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically-acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically-acceptable solid solvent includes, without limitation, Menthol and PEG polymers above about 20,000 g/mol.

Aspects of the present specification disclose, in part, a pharmaceutically-acceptable adjuvant. An adjuvant is a pharmacological agent that modifies the effect of other agents, such as, e.g., a therapeutic compound disclosed herein. In addition, an adjuvant disclosed herein may be used as a solvent that dissolves a therapeutic compound disclosed herein, forming a adjuvant solution. An adjuvant disclosed herein facilitates delivery of a therapeutic compound in a manner that more effectively normalizes lipid levels and/or inhibits a pro-inflammatory response. In one embodiment, an adjuvant disclosed herein facilitates the delivery of a therapeutic compound disclosed herein into macrophages.

A pharmaceutical composition disclosed herein may comprise a pharmaceutically-acceptable adjuvant in an amount sufficient to mix with a solution disclosed herein or an emulsion disclosed herein. In other aspects of this embodiment, a pharmaceutical composition disclosed herein may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition disclosed herein may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition disclosed herein may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically-acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a wax, a fatty acid ester, a fatty acid salt, a fatty alcohol, a glyceride (mono-, di- or tri-glyceride), a phospholipids, a glycol ester, a sucrose ester, a glycerol oleate derivative, a medium chain triglyceride, or a mixture thereof.

A lipid useful in the pharmaceutical compositions disclosed herein may be a pharmaceutically-acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid (8:0), pelargonic acid (9:0), Capric acid (10:0), Undecylic acid (11:0), Lauric acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and Hexatriacontylic acid (36:0).

In an embodiment, an adjuvant may be a pharmaceutically-acceptable saturated or unsaturated fatty acid. In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

In aspects of this embodiment, a pharmaceutically-acceptable saturated or unsaturated fatty acid is liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20° C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., about −15° C. to about 0° C.

In another embodiment, an adjuvant may comprise one kind of pharmaceutically-acceptable fatty acid. In aspects of this embodiment, an adjuvant may comprise only palmitic acid, only stearic acid, only oleic acid, only linoleic acid, or only linolenic acid.

In another embodiment, an adjuvant may comprise a plurality of different pharmaceutically-acceptable fatty acids. In aspects of this embodiment, an adjuvant may comprise, e.g., two or more different fatty acids, three or more different fatty acids, four or more different fatty acids, five or more different fatty acids, or six or more different fatty acids.

In other aspects of this embodiment, an adjuvant may comprise two or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid and/or stearic acid and/or oleic acid:linolenic acid and/or linoleic acid of, e.g., at least 2:1, at least 3:1, at least 4:1, at least 5:1, at least 6:1, at least 7:1, at least 8:1, at least 9:1, at least 10:1, at least 15:1, or at least 20:1. In yet other aspects of this embodiment, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

In other aspects of this embodiment, an adjuvant may comprise four or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid:stearic acid:linolenic acid:linoleic acid of, e.g., 10:10:1:1, 9:9:1:1, 8:8:1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid:stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions disclosed herein may be a pharmaceutically-acceptable omega fatty acid. Non-limiting examples of an omega fatty acid include omega-3, omega-6, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (22:5), Clupanodonic acid (22:5), Docosahexaenoic acid (22:6), Tetracosapentaenoic acid (24:5), Tetracosahexaenoic acid (Nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, Linoleic acid (18:2), Gamma-linolenic acid (18:3), Calendic acid (18:3), Eicosadienoic acid (20:2), Dihomo-gamma-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5). Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, oleic acid (18:1), Elaidic acid (18:1), Eicosenoic acid (20:1), Mead acid (20:3), Erucic acid (22:1), and Nervonic acid (24:1).

A lipid useful in the pharmaceutical compositions disclosed herein may be a pharmaceutically-acceptable oil. An oil includes any fatty acid that is liquid at normal room temperature, such as, e.g. about 20° C. In contrast, a fat includes any fatty acid that is solid at normal room temperature, such as, e.g. about 20° C. An oil suitable as a lipid useful in the pharmaceutical compositions disclosed herein, may be a natural oil or a vegetable oil. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, walnut oil, wheat germ oil, or a mixture thereof. Each of these oils is commercially available from a number of sources well recognized by those skilled in the art.

An oil is typically a mixture of various fatty acids. For example, Rapeseed oil, obtained from the seeds of *Brassica napus*, includes both omega-6 and omega-3 fatty acids in a ratio of about 2:1. As another example, linseed oil, obtained from the seeds of *Linum usitatissimum*, includes about 7% palmitic acid, about 3.4-4.6% stearic acid, about 18.5-22.6% oleic acid, about 14.2-17% linoleic acid, and about 51.9-55.2% α-linolenic acid. In aspects of this embodiment, a pharmaceutical composition comprises an oil including at least two different fatty acids, at least three different fatty acids, at least four different fatty acids, at least five different fatty acids, or at least six different fatty acids.

A lipid useful in the pharmaceutical compositions disclosed herein may be a pharmaceutically-acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

Aspects of the present specification disclose, in part, a pharmaceutically-acceptable stabilizing agent. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically-acceptable stabilizing agent may comprise a pharmaceutically-acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

In an aspect of this embodiment, an emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

In an aspect of this embodiment, an emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (NEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

In an aspect of this embodiment, an emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, *Maackia anurensis* leukoagglutinin, *Maackia anurensis* hemoagglutinin, *Ulex europaeus* agglutinin, and *Aleuria aurantia* lectin.

In an aspect of this embodiment, an emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline; one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

In one embodiment, a pharmaceutically-acceptable stabilizing agent does not comprise a pharmaceutically-acceptable emulsifying agent.

In another embodiment, a pharmaceutical composition does not comprise a pharmaceutically-acceptable emulsifying agent.

The pharmaceutical compositions disclosed herein act as a delivery system that enable a therapeutic compound disclosed herein to be more effectively delivered or targeted to a cell type, tissue, organ, or region of the body in a manner that more effectively normalizes lipid levels and/or inhibits a pro-inflammatory response. This modulation and/or inhibition results in an improved treatment of a cardiovascular disease. For example, a pharmaceutical composition disclosed herein may facilitate the delivery of a therapeutic compound disclosed herein into macrophages. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration of the pharmaceutical compositions disclosed herein are processed into micelles while in the gastrointestinal tract, absorbed by enterocytes and assembled into nascent chylomicrons, remain associated with chylomicron remnants taken up by the liver, and ultimately loaded into macrophages.

Aspects of the present specification disclose, in part, a method of preparing a pharmaceutical composition disclosed herein. A method disclosed herein comprises the step of contacting a pharmaceutically-acceptable adjuvant disclosed herein with a therapeutic compound disclosed herein under conditions which allow the therapeutic compound to dissolve in the pharmaceutically-acceptable adjuvant, thereby forming a pharmaceutical composition disclosed herein.

Aspects of the present specification disclose, in part, a method of preparing a pharmaceutical composition disclosed herein. A method disclosed herein comprises the steps of a) contacting a pharmaceutically-acceptable solvent disclosed herein with a therapeutic compound disclosed herein under conditions which allow the therapeutic compound to dissolve in the pharmaceutically-acceptable solvent, thereby forming a solution; and b) contacting the solution formed in step (a) with a pharmaceutically-acceptable adjuvant disclosed herein under conditions which allow the formation of a pharmaceutical composition. The methods of preparing disclosed herein may further comprise a step (c) of removing the pharmaceutically-acceptable solvent from the pharmaceutical composition.

The amount of a therapeutic compound that is contacted with the pharmaceutically-acceptable solvent in step (a) of the method may be in any amount desired. Factors used to determine the amount of a therapeutic compound used include, without limitation, the final amount the therapeutic compound desired in the pharmaceutical composition, the desired concentration of a therapeutic compound in the solution, the hydrophobicity of the therapeutic compound, the lipophobicity of the therapeutic compound, the temperature under which the contacting step (a) is performed, and the time under which the contacting step (a) is performed The volume of a pharmaceutically-acceptable solvent used in step (a) of the method may be any volume desired. Factors used to determine the volume of a pharmaceutically-acceptable solvent used include, without limitation, the final amount of a pharmaceutical composition desired, the desired concentration of a therapeutic compound in the solution, the hydrophobicity of the therapeutic compound, and the lipophobicity of the therapeutic compound.

In aspects of this embodiment, the amount of a therapeutic compound that is contacted with the solvent in step (a) may be, e.g., at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In other aspects of this embodiment, the amount of a therapeutic compound that is contacted with the solvent in step (a) may be in the range of, e.g., about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In other aspects of this embodiment, the amount of a therapeutic compound that is dissolved in the solvent in step (a) may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, or about 200 mg to about 1,500 mg.

Step (a) may be carried out at room temperature, in order to allow a therapeutic compound to dissolve fully in the pharmaceutically-acceptable solvent. However, in other embodiments of the method, step (a) may be carried out at a temperature that is greater than room temperature, e.g., greater than 21° C., greater than 25° C., greater than 30° C., greater than 35° C. or greater than 37° C. In certain cases, Step (a) may be carried out at temperatures below room temperature, in order to allow a therapeutic compound to dissolve fully in solvent. However, in other embodiments of the method, step (a) may be carried out at a temperature that is less than room temperature, e.g., less than 10° C., greater than 5° C., greater than 0° C., greater than −10° C. or greater than −20° C. The contacting in Step (a) may comprise mixing the therapeutic compound and the pharmaceutically-acceptable solvent, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the solvent.

After contacting, the concentration of a therapeutic compound disclosed herein in the solution may be in any concentration desired. In aspects of this embodiment, the concentration of a therapeutic compound disclosed herein in the solution may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the concentration of a therapeutic compound disclosed herein in the solution may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

The volume of a pharmaceutically-acceptable adjuvant used in step (b) of the method may be any volume desired. Factors used to determine the volume of a pharmaceutically-acceptable adjuvant used include, without limitation, the final amount of a pharmaceutical composition desired, the desired concentration of a therapeutic compound in the pharmaceutical composition, the ratio of solvent:adjuvant used, and the miscibility of solvent and adjuvant.

In aspects of this embodiment, the ratio of solution:adjuvant may be, e.g., at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of solution:adjuvant may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

Step (b) may be carried out at room temperature, in order to allow the solution comprising the therapeutic compound to form the pharmaceutical composition. However, in other embodiments of the method, step (b) may be carried out at a temperature that is greater than room temperature, e.g., greater than 21° C., greater than 25° C., greater than 30° C., greater than 35° C. or greater than 37° C. In certain cases, Step (b) may be carried out at temperatures below room temperature, in order to allow a therapeutic compound to dissolve fully in a pharmaceutically-acceptable solvent. However, in other embodiments of the method, step (b) may be carried out at a temperature that is less than room temperature, e.g., less than 10° C., greater than 5° C., greater than 0° C., greater than –10° C. or greater than –20° C. The contacting in Step (b) may comprise mixing the solution and the pharmaceutically-acceptable adjuvant, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the pharmaceutical composition is formed.

In Step (c), the solvent removal from a pharmaceutical composition may be accomplished using one of a variety of procedures known in the art, including, without limitation, evaporation, dialyzation, distillation, lypholization, and filtration. These removal procedures may be done under conditions of ambient atmosphere, under low pressure, or under a vacuum.

In one embodiment, Step (c) may result in the complete removal of a pharmaceutically-acceptable solvent from the pharmaceutical composition disclosed herein. In aspects of this embodiment, Step (c) may result in, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 93%, at least 95%, at least 97%, or at least 99% removal of a pharmaceutically-acceptable solvent from the pharmaceutical composition disclosed herein.

Step (c) is conducted at a temperature that allows for the evaporation of a pharmaceutically-acceptable solvent disclosed herein, and as such, an evaporation temperature is solvent dependant. Factors which influence an evaporation temperature of a solvent disclosed herein include, without limitation, the particular solvent used, the amount of solvent present, the particular therapeutic compound present, the particular adjuvant present, the stability of the therapeutic compound present, the reactivity of the therapeutic compound present, the particular atmospheric pressure used, the time desired for complete evaporation. Generally, a pharmaceutical composition will require heating if the evaporation step is conducted at ambient pressure, e.g., 1 atm. However, under high vacuum conditions, the evaporation step may be conducted at temperatures below ambient temperature, e.g., less than 22° C.

In one embodiment, removal of solvent from the pharmaceutical composition disclosed herein may be carried out at ambient atmospheric pressure and at a temperature above ambient temperature. In aspects of this embodiment, removal of solvent from the pharmaceutical composition disclosed herein may be carried out at ambient atmospheric pressure and at a temperature of, e.g., more than 25° C., more than 30° C., more than 35° C., more than 40° C., more than 45° C., more than 50° C., more than 55° C., more than 60° C., more than 65° C., more than 70° C., more than 80° C., or more than 25° C. In other aspects of this embodiment, removal of solvent from the pharmaceutical composition disclosed herein may be carried out at ambient atmospheric pressure and at a temperature in a range of, e.g., about 25° C. to about 100° C., about 25° C. to about 95° C., about 25° C. to about 90° C., about 25° C. to about 85° C., about 25° C. to about 80° C., about 25° C. to about 75° C., about 25° C. to about 70° C., about 25° C. to about 65° C., or about 25° C. to about 60° C.

In another embodiment, removal of solvent from the pharmaceutical composition disclosed herein may be carried out under vacuum and at a temperature below ambient temperature. In aspects of this embodiment, removal of solvent from the pharmaceutical composition disclosed herein may be carried out under vacuum and at a temperature of, e.g., less than 20° C., less than 18° C., less than 16° C., less than 14° C., less than 12° C., less than 10° C., less than 8° C., less than 6° C., less than 4° C., less than 2° C., or less than 0° C. In other aspects of this embodiment, removal of solvent from the pharmaceutical composition disclosed herein may be carried out under vacuum and at a temperature in a range of, e.g., about −20° C. to about 20° C., about −20° C. to about 18° C., about −20° C. to about 16° C., about −20° C. to about 14° C., about −20° C. to about 12° C., about −20° C. to about 10° C., about −20° C. to about 8° C., about −20° C. to about 6° C., about −20° C. to about 4° C., about −20° C. to about 2° C., about −20° C. to about 0° C., about −15° C. to about 20° C., about −10° C. to about 20° C., about −5° C. to about 20° C., about 0° C. to about 20° C., about −10° C. to about 20° C., about −10° C. to about 18° C., about −10° C. to about 16° C., about −10° C. to about 14° C., about −10° C. to about 12° C., about −10° C. to about 10° C., about −10° C. to about 8° C., about −10° C. to about 6° C., about −10° C. to about 4° C., about −10° C. to about 2° C., or about −10° C. to about 0° C.

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be a liquid formulation or a solid or semi-solid formulation. A liquid formulation can be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher. In other aspects of this embodiment, a pharmaceutical composition disclosed herein may be formulated to be a liquid at a temperature of, e.g., A solid or semi-solid formulation disclosed herein takes advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature ($T_m$) of about −11° C., linoleic acid has a $T_m$ of about −5° C., oleic acid has a $T_m$ of about 16° C., palmitic acid has a $T_m$ of about 61-62° C., and Stearic acid has a $T_m$ of about 67-72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

In an embodiment, a pharmaceutical composition disclosed herein is solid at room temperature. In aspects of this embodiment, a pharmaceutical composition disclosed herein may be formulated to be a solid at a temperature of, e.g., about 35° C. or lower, about 33° C. or lower, about 31° C. or lower, about 29° C. or lower, about 27° C. or lower, about 25° C. or lower, about 23° C. or lower, about 21° C. or lower, about 19° C. or lower, about 17° C. or lower, about 15° C. or lower, about 12° C. or lower, about 10° C. or lower, about 8° C. or lower, about 6° C. or lower, v 4° C. or lower, or about 0° C. or lower.

In other aspects of this embodiment, a pharmaceutical composition disclosed has a melting point temperature of, e.g., 5° C. or higher, 10° C. or higher, 15° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, or 35° C. or higher. In other aspects of this embodiment, a pharmaceutical composition disclosed has a melting point temperature in the range of, e.g., about 5° C. to about 24° C., about 10° C. to about 24° C. about 22° C. to about 24° C., about 23° C. to about 25° C., about 24° C. to about 26° C., about 25° C. to about 27° C., about 26° C. to about 28° C., about 27° C. to about 29° C., about 28° C. to about 30° C., about 29° C. to about 31° C., about 30° C. to about 32° C., about 31° C. to about 33° C., about 32° C. to about 34° C., or about 33° C. to about 35° C. In other aspects of this embodiment, a pharmaceutical composition disclosed has a melting point temperature in the range of, e.g., about 22° C. to about 26° C., about 24° C. to about 28° C., about 26° C. to about 30° C., about 28° C. to about 32° C., or about 30° C. to about 34° C.

Aspects of the present specification disclose, in part, a method of treating an individual with a cardiovascular disease. In one embodiment, the method comprises the step of administering to an individual in need thereof a pharmaceutical composition disclosed herein, wherein administration reduces a symptom associated with the cardiovascular disease, thereby treating the individual.

Aspects of the present specification disclose, in part, treating an individual suffering from a cardiovascular disease. As used herein, the term "treating," refers to reducing or eliminating in an individual a clinical symptom of a cardiovascular disease; or delaying or preventing in an individual the onset of a clinical symptom of a cardiovascular disease. For example, the term "treating" can mean reducing a symptom of a condition characterized by a cardiovascular disease by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a cardiovascular disease are well known and can be determined by a person of ordinary skill in the art by taking into account factors, including, without limitation, the location of the cardiovascular disease, the cause of the cardiovascular disease, the severity of the cardiovascular disease, and/or the tissue or organ affected by the cardiovascular disease. Those of skill in the art will know the appropriate symptoms or indicators associated with a specific type of cardiovascular disease and will know how to determine if an individual is a candidate for treatment as disclosed herein.

Cardiovascular disease is any of a number of specific diseases that affect the heart itself and/or the blood vessel system, especially the veins and arteries leading to and from the heart. Known and/or associated causes of a cardiovascular disease include, without limitation, unhealthy ratios of the two smallest lipoproteins LDL and HDL, hyperlipidemia, elevated blood glucose levels, upper normal and high blood pressure, Lp-PLA2, lipoprotein(a) and hyperhomocysteinemia. Symptoms of a cardiovascular disorder affecting the heart include, without limitation, chest pain, chest discomfort, and pain in one or both arms, one or both shoulders, neck, jaw, or back, shortness of breath, dizziness, faster heartbeats, nausea, abnormal heartbeats, fatigue, and/or myocardial infarction. Symptoms of a cardiovascular disorder affecting the brain include, without limitation, sudden numbness or weakness of the face, one or both arms, or one or both legs, sudden confusion or trouble speaking or understanding speech, sudden trouble seeing in one or both eyes, sudden dizziness, difficulty walking, or loss of balance or coordination, and/or sudden severe headache with no known cause. Symptoms of a cardiovascular disorder affecting one or both leg, pelvis, one or both arms, and/or shoulder include, without limitation, muscle pain, muscle cramp, cold sensation in one or both feet and/or toes, one or both hands and/or fingers, and/or numbness or weakness in one or both feet and/or toes, one or both hands and/or fingers.

There are more than 60 types of cardiovascular disease including, without limitation, a hyperlipidemia, a coronary heart disease, an atherosclerosis, a peripheral vascular disease, a cardiomyopathy, a vasculitis, an inflammatory heart disease, an ischemic heart disease, a congestive heart failure, a hypertensive heart disease, a valvular heart disease, a hypertension, myocardial infarction, a diabetic cardiac conditions, an aneurysm; an embolism, a dissection, a pseudoaneurysm, a vascular malformation, a vascular nevus, a thrombosis, a varicose vein, and a stroke.

In one embodiment, a cardiovascular disease comprises a hyperlipidemia. A hyperlipidemia (or hyperlipoproteinemia) refers to a condition characterized by abnormally elevated levels of lipids and/or lipoproteins in the blood. Hyperlipidemias may be classified as familial (or primary) when caused by specific genetic abnormalities, acquired (or secondary) when resulting from another underlying disorder, or idiopathic, when of unknown cause. Hyperlipidemias may also be classified based on which types of lipids and/or lipoproteins are elevated. Non-limiting examples of a hyperlipidemia include dyslipidemia, hypercholesterolemia, hyperglyceridemia, hypertriglyceridemia, hyperlipoproteinemia, and hyperchylomicronemia, and combined hyperlipidemia. Hyperlipoproteinemia include, e.g., hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, and hyperlipoproteinemia type V.

In another embodiment, a cardiovascular disease comprises a coronary heart disease. A coronary heart disease refers to a condition characterized by failure of the coronary circulation to supply adequate blood flow to cardiac muscle and surrounding tissue. Typically caused by the narrowing or blockage of the coronary artery, such as, e.g., an atherosclerotic coronary artery disease, a coronary vasospasm, and/or a coronary stenosis. Chest pain and myocardial infarction are common symptoms of and conditions caused by coronary heart disease.

In another embodiment, a cardiovascular disease comprises a vascular occlusive disease (VOD). A VOD refers to a condition characterized by an obstruction of a blood vessel. A VOD includes, without limitation, an atherosclerosis, a peripheral vascular disease, and a stenosis.

In an aspect of this embodiment, a VOD comprises an atherosclerosis. An atherosclerosis refers to a condition characterized by a buildup of cholesterol and fatty deposits (called plaques) on the inner walls of the arteries. These plaques can restrict blood flow to the heart muscle by physically clogging the artery or by causing abnormal artery tone and function. Rupture of atherosclerotic plaque is the most common cause of an ischemia.

In an aspect of this embodiment, a VOD comprises a peripheral vascular disease (PVD). Peripheral vascular disease (PVD), also known as peripheral arterial disease (PAD) or peripheral artery occlusive disease (PAOD), refers to a condition characterized by an obstruction of large arteries not within the coronary, aortic arch vasculature, or brain. PVD can result from atherosclerosis, an inflammatory processes leading to stenosis, an embolism, or thrombus formation. It causes either acute or chronic ischemia. PVD also includes a subset of diseases classified as microvascular diseases resulting from episodic narrowing of the arteries, such as, e.g., Raynaud's phenomenon, or widening of the arteries, such as, e.g., a vascular spasm. Symptoms of PVD include, without limitation, pain, weakness, numbness, or cramping in muscles due to decreased blood flow, sores, wounds, or ulcers that heal slowly or not at all, blueness or paleness in limb, coolness in limb, diminished hair and nail growth on affected limb and digits. About 20% of patients with mild PAD may be asymptomatic.

In another embodiment, a cardiovascular disease comprises a cardiomyopathy. A cardiomyopathy refers to a condition characterized by the deterioration of myocardium function. Symptoms and signs may mimic those of almost any form of heart disease and include chest pain and EKG abnormalities. A mild cardiomyopathy is frequently asymptomatic. A more severe case is associated with heart failure, arrhythmias, systemic embolization and/or sudden cardiac death. A cardiomyopathy may be classified functionally, as involving dilation, hypertrophy, or restriction.

A cardiomyopathy may also be classified as either extrinsic or intrinsic. An extrinsic cardiomyopathy refers to a cardiomyopathy where the primary pathology is outside the myocardium itself. For example, an extrinsic cardiomyopathy may be caused by a metabolic/storage disorder, an endocrine disorder, a neuromuscular disorder, a nutritional disorder, an inflammation, a toxicity (including drug and alcohol), an ischemia, and/or an infection (including Hepatitis C). Non-limiting examples of extrinsic cardiomyopathies include acromegaly, alcoholic cardiomyopathy, amyloidosis, Chagas disease, chemotherapy, diabetic cardiomyopathy, hemochromatosis, hypertensive cardiomyopathy, hyperthyroidism, inflammatory cardiomyopathy, ischemic cardiomyopathy, muscular dystrophy, valvular cardiomyopathy, a cardiomyopathy secondary to a systemic metabolic disease, a cardiomyopathy secondary to a systemic nutritional disease, a coronary artery disease, and a congenital heart disease.

An intrinsic cardiomyopathy refers to a cardiomyopathy where there is a weakness in the muscle of the heart that is not due to an identifiable external cause, i.e., of unknown origin. Intrinsic cardiomyopathies comprise a variety of disease states due to its idiopathic nature and may be classified as genetic, mixed or acquired. Non-limiting examples of intrinsic cardiomyopathies include dilated cardiomyopathy (DCM), hypertrophic cardiomyopathy (HCM or HOCM), arrhythmogenic right ventricular cardiomyopathy (ARVC), restrictive cardiomyopathy (RCM), noncompaction cardiomyopathy, isolated ventricular non-compaction, mitochondrial myopathy, Takotsubo cardiomyopathy, and Loeffler endocarditis.

In another embodiment, a cardiovascular disease comprises a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, thrombophlebitis, Wegener's granulomatosis, and vasculitis secondary to connective tissue disorders like systemic lupus erythematosus (SLE), rheumatoid arthritis (RA), relapsing polychondritis, Behçet's disease, or other connective tissue disorders, vasculitis secondary to viral infection.

In another embodiment, a cardiovascular disease comprises an inflammatory heart disease. An inflammatory heart disease refers to a condition characterized by inflammation of the heart muscle and/or the tissue surrounding it. Non-limiting examples of inflammatory heart disease include endocarditis, inflammatory cardiomegaly, and myocarditis.

In another embodiment, a cardiovascular disease comprises an ischemic heart disease. Ischemic heart disease, or myocardial ischemia, refers to a condition characterized by reduced blood supply of the heart muscle, usually due to a narrowing or blockage of a coronary artery. Symptoms of ischemic heart disease include chest pain on exertion, in cold weather or emotional situations, acute chest pain, acute coronary syndrome, unstable angina, myocardial infarction, heart failure, difficulty in breathing or swelling of the extremities.

In another embodiment, a cardiovascular disease comprises a congestive heart failure. A congestive heart failure, or congestive cardiac failure, refers to a condition characterized by a heart abnormality that cannot result from any structural or functional cardiac disorder that impairs the ability of the heart to fill with or pump a sufficient amount of blood throughout the body.

In another embodiment, a cardiovascular disease comprises a hypertensive heart disease. A hypertensive heart disease refers to a condition characterized by high blood pressure, especially localized high blood pressure. Conditions that can be caused by hypertensive heart disease include, without limitation, left ventricular hypertrophy, coronary heart disease, congestive heart failure, hypertensive cardiomyopathy, and cardiac arrhythmias.

In another embodiment, a cardiovascular disease comprises a valvular heart disease. A valvular heart disease refers to a condition characterized by a malfunction of one or more valves of the heart. Major heart valves which may be affected by valvular heart disease, including, without limitation, tricuspid valve, right aortic valve, mitral valve, and left aortic valve.

A composition or compound is administered to an individual. An individual is typically a human being. Typically, any individual who is a candidate for a conventional cardiovascular disease treatment is a candidate for a cardiovascular disease treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a cardiovascular disease refers to the minimum dose of a therapeutic compound disclosed herein necessary to achieve the desired therapeutic effect and includes a dose sufficient to reduce a symptom associated with a cardiovascular disease. The effectiveness of a therapeutic compound disclosed herein in treating a cardiovascular disease is determined by observing an improvement in an individual based upon one or more clinical symptoms, and/or physiological indicators associated with the condition. An improvement in a cardiovascular disease also can be indicated by a reduced need for a concurrent therapy.

The appropriate effective amount of a therapeutic compound disclosed herein to be administered to an individual for a particular cardiovascular disease can be determined by a person of ordinary skill in the art by taking into account factors, including, without limitation, the type of cardiovascular disease, the location of the cardiovascular disease, the cause of the cardiovascular disease, the severity of the cardiovascular disease, the degree of relief desired, the duration of relief desired, the particular therapeutic compound used, the rate of excretion of the therapeutic compound used, the pharmacodynamics of the therapeutic compound used, the nature of the other compounds to be included in the composition, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

In aspects of this embodiment, a therapeutically effective amount of a therapeutic compound disclosed herein reduces a symptom associated with a cardiovascular disease by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a cardiovascular disease by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a cardiovascular disease by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a cardiovascular disease may comprise a one-time administration of an effective dose of a pharmaceutical composition disclosed herein. Alternatively, treatment of a cardiovascular disease may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, upon administration to an individual, a pharmaceutical composition comprising a therapeutic compound disclosed herein results in a bio-distribution of the therapeutic compound different than a bio-distribution of the therapeutic compound included in the same pharmaceutical composition, except without an adjuvant disclosed herein.

In another embodiment, upon administration to an individual, a therapeutic compound of the pharmaceutical composition disclosed herein is delivered to a macrophage. Macrophages are one of the key cell types believed to be involved in the control of the inflammation response. The resultant high level of a therapeutic compound having an activity that normalizes lipid levels and/or anti-inflammatory activity present in the macrophages results in a clinically effective treatment of cardiovascular disease. In an aspect of this embodiment, upon administration to an individual, a therapeutically effective amount of a therapeutic compound of the pharmaceutical composition disclosed herein is preferentially delivered to a macrophage. In other aspect of this embodiment, upon administration to an individual, a therapeutic compound of the pharmaceutical composition disclosed herein is substantially delivered to a macrophage. In yet other aspect of this embodiment, upon administration to an individual, the amount of a therapeutic compound of the pharmaceutical composition disclosed herein delivered to a macrophage is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a macrophage is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a pharmaceutical composition disclosed herein reduces gastric irritation. In an aspect of this embodiment, a pharmaceutical composition disclosed herein substantially reduces gastric irritation. In yet another embodiment, upon administration to an individual, a pharmaceutical composition disclosed herein reduces gastric irritation when compared to the same pharmaceutical composition disclosed herein, except without the pharmaceutically-acceptable adjuvant. In an aspect of this embodiment, a pharmaceutical composition disclosed herein substantially reduces gastric irritation when compared to the same pharmaceutical composition disclosed herein, except without the pharmaceutically-acceptable adjuvant. In other aspects of this embodiment, a pharmaceutical composition disclosed herein reduces gastric irritation by, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In yet other aspects of this embodiment, a pharmaceutical composition disclosed herein reduces gastric irritation in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70%.

In another embodiment, upon administration to an individual, a pharmaceutical composition disclosed herein reduces intestinal irritation. In an aspect of this embodiment, a pharmaceutical composition disclosed herein substantially reduces intestinal irritation. In yet another embodiment, upon administration to an individual, a pharmaceutical composition disclosed herein reduces intestinal irritation when compared to the same pharmaceutical composition disclosed herein, except without the pharmaceutically-acceptable adjuvant. In an aspect of this embodiment, a pharmaceutical composition disclosed herein substantially reduces intestinal irritation when compared to the same pharmaceutical composition disclosed herein, except without the pharmaceutically-acceptable adjuvant. In other aspects of this embodiment, a pharmaceutical composition disclosed herein reduces intestinal irritation by, e.g., at least 5%, at least 10%, at least 20%, at least 30%, at least 40%, at least 50%, at least 60%, at least 70%, at least 80%, at least 90%, or at least 100% when compared to the same pharmaceutical composition disclosed herein, except without the pharmaceutically-acceptable adjuvant. In yet other aspects of this embodiment, a pharmaceutical composition disclosed herein reduces intestinal irritation by, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% when compared to the same pharmaceutical composition disclosed herein, except without the pharmaceutically-acceptable adjuvant.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present invention can also be described as follows:
1. A pharmaceutical composition comprising: a) a therapeutic compound, wherein the therapeutic compound has an activity that normalizes lipid levels; and b) a pharmaceutically-acceptable adjuvant.
2. The pharmaceutical composition according to embodiment 1, wherein the composition further comprises a pharmaceutically-acceptable solvent.
3. A pharmaceutical composition comprising: a) a therapeutic compound, wherein the therapeutic compound has an activity that normalizes lipid levels; b) a pharmaceutically-acceptable solvent; and c) a pharmaceutically-acceptable adjuvant.
4. A pharmaceutical composition comprising: a) a therapeutic compound, wherein the therapeutic compound has an activity that normalizes lipid levels; b) a pharmaceutically-acceptable solvent; and c) a pharmaceutically-acceptable adjuvant, wherein the ratio of the pharmaceutically-acceptable solvent to pharmaceutically-acceptable adjuvant is in a range from about 0:1 to about 1:25.
5. The pharmaceutical composition according to embodiment 2 or 3, wherein the ratio of the pharmaceutically-acceptable solvent to pharmaceutically-acceptable adjuvant is in a range from about 0:1 to about 1:25.
6. The pharmaceutical composition according to embodiments 1-5, wherein the activity that normalizes lipid levels has an anti-hyperlipidemia activity.
7. The pharmaceutical composition according to embodiment 6, wherein the anti-hyperlipidemia activity reduces the levels of VLDL, IDL, LDL, or a combination thereof by at least 10%.
8. The pharmaceutical composition according to embodiment 7, wherein the anti-hyperlipidemia activity increases the level of HDL by, e.g., at least 2%
9. The pharmaceutical composition according to embodiments 1-8, wherein the activity that normalizes lipid levels reduces the level of an inflammation inducing prostaglandin.
10. The pharmaceutical composition according to embodiment 9, wherein the level of the inflammation inducing prostaglandin is reduced by at least 10%.
11. The pharmaceutical composition according to embodiments 1-10, wherein the activity that normalizes lipid levels stimulates a PPAR signaling pathway.
12. The pharmaceutical composition according to embodiment 11, wherein the PPAR signaling pathway is stimulated by at least 10%.
13. The pharmaceutical composition according to embodiments 1-12, wherein the activity that normalizes lipid levels induces apoptosis of Macrophage M1 cells, promotes differentiation of Macrophage M2 cells, or both.
14. The pharmaceutical composition according to embodiments 1-13, wherein the activity that normalizes lipid levels reduces the levels of Interferon-gamma (IFNγ), Tumor necrosis factor-alpha (TNF-α), Interleukin-12 (IL-12), or a combination thereof released from Th1 cells, increases the levels of IL-10 released from a Th2 cell, or both.
15. The pharmaceutical composition according to embodiment 14, wherein the levels of IFNγ, TNF-α, IL-12, or a combination thereof released from a Th1 cell are reduced by at least 10%.
16. The pharmaceutical composition according to embodiment 14, wherein the levels of IL-10 released from a Th2 cell are increased by at least 10%.
17. The pharmaceutical composition according to embodiments 1-16, wherein the activity that normalizes lipid levels reduces the level of an inflammation inducing molecule.
18. The pharmaceutical composition according to embodiment 17, wherein the inflammation inducing molecule comprises substance P (SP), calcitonin gene-related peptide (CGRP), glutamate, or a combination thereof.
19. The pharmaceutical composition according to embodiments 1-18, wherein the therapeutic compound has a log P value indicating that the compound is soluble in an organic solvent.
20. The pharmaceutical composition according to embodiments 1-19, wherein the therapeutic compound has a log P value of more than 1.0.
21. The pharmaceutical composition according to embodiments 1-19, wherein the therapeutic compound has a log P value of more than 2.0.
22. The pharmaceutical composition according to embodiments 1-21, wherein the therapeutic compound has a polar surface area that is hydrophobic.
23. The pharmaceutical composition according to embodiments 1-22, wherein the therapeutic compound has a polar surface area that is less than 8.0 nm$^2$.

24. The pharmaceutical composition according to embodiments 1-22, wherein the therapeutic compound has a polar surface area that is less than 6.0 nm².

25. The pharmaceutical composition according to embodiments 1-24, wherein the therapeutic compound comprises a non-steroidal anti-inflammatory drug (NSAID).

26. The pharmaceutical composition according to embodiment 25, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor or a combination thereof.

27. The pharmaceutical composition according to embodiments 1-26, wherein the therapeutic compound comprises a PPARγ agonist.

28. The pharmaceutical composition according to embodiment 27, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.

29. The pharmaceutical composition according to embodiments 1-28, wherein the therapeutic compound comprises a nuclear receptor binding agent.

30. The pharmaceutical composition according to embodiment 29, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.

31. The pharmaceutical composition according to embodiments 1-30, wherein the therapeutic compound comprises an anti-hyperlipidemic agent.

32. The pharmaceutical composition according to embodiment 31, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.

33. The pharmaceutical composition according to embodiment 31, wherein the fibrate comprises Bezafibrate, Ciprofibrate, Clofibrate, Gemfibrozil, Fenofibrate, or a combination thereof.

34. The pharmaceutical composition according to embodiment 31, wherein the statin comprises Atorvastatin, Fluvastatin, Lovastatin, Pitavastatin, Pravastatin, Rosuvastatin, Simvastatin, or a combination thereof.

35. The pharmaceutical composition according to embodiment 31, wherein the niacin comprises acipimox, niacin, nicotinamide, vitamin B3, or a combination thereof.

36. The pharmaceutical composition according to embodiment 31, wherein the bile acid sequestrant comprises Cholestyramine, Colesevelam, Colestipol, or a combination thereof.

37. The pharmaceutical composition according to embodiment 31, wherein the cholesterol absorption inhibitor comprises Ezetimibe, a phytosterol, a sterol, a stanol, or a combination thereof.

38. The pharmaceutical composition according to embodiment 31, wherein the fat absorption inhibitor comprises Orlistat 39. The pharmaceutical composition according to embodiment 31, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.

40. The pharmaceutical composition according to embodiments 1-39, wherein the therapeutic compound comprises an ester of a therapeutic compound.

41. The pharmaceutical composition according to embodiments 1-40, wherein the therapeutic compound comprises an ester of a therapeutic compound according to embodiments 25-39.

42. The pharmaceutical composition according to embodiments 1-41, wherein the pharmaceutically-acceptable solvent is less than about 20% (v/v).

43. The pharmaceutical composition according to embodiments 1-42, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.

44. The pharmaceutical composition according to embodiments 1-43, wherein the pharmaceutically-acceptable solvent comprises a pharmaceutically-acceptable alcohol.

45. The pharmaceutical composition according to embodiment 44, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.

46. The pharmaceutical composition according to embodiment 44, wherein the pharmaceutically-acceptable alcohol comprises a $C_{1-20}$ alcohol.

47. The pharmaceutical composition according to embodiment 44, wherein the pharmaceutically-acceptable alcohol comprises methanol, ethanol, propanol, butanol, pentanol, 1-hexadecanol, or a combination thereof.

48. The pharmaceutical composition according to embodiments 1-47, wherein the pharmaceutically-acceptable solvent comprises a pharmaceutically-acceptable ester of pharmaceutically-acceptable alcohol and an acid.

49. The pharmaceutical composition according to embodiment 48, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.

50. The pharmaceutical composition according to embodiments 1-49, wherein the pharmaceutically-acceptable solvent comprises a pharmaceutically-acceptable polyethylene glycol (PEG) polymer.

51. The pharmaceutical composition according to embodiment 50, wherein the pharmaceutically-acceptable polyethylene glycol (PEG) polymer is less than about 2,000 g/mol.

52. The pharmaceutical composition according to embodiment 50, wherein the pharmaceutically-acceptable polyethylene glycol (PEG) polymer is more than about 2,000 g/mol.

53. The pharmaceutical composition according to embodiments 1-52, wherein the pharmaceutically-acceptable solvent comprises a pharmaceutically-acceptable glyceride.

54. The pharmaceutical composition according to embodiment 53, wherein the pharmaceutically-acceptable glyceride comprises a monoglyceride, a diglyceride, a triglyceride, an acetylated monoglyceride, an acetylated diglyceride, an acetylated triglyceride, or a combination thereof.
55. The pharmaceutical composition according to embodiments 1-54, wherein the pharmaceutically-acceptable solvent is a liquid at 20° C.
56. The pharmaceutical composition according to embodiments 1-54, wherein the pharmaceutically-acceptable solvent is a solid at 20° C.
57. The pharmaceutical composition according to embodiment 56, wherein the pharmaceutically-acceptable solid solvent comprises menthol.
58. The pharmaceutical composition according to embodiments 1-57, wherein the adjuvant is at least 80% (v/v).
59. The pharmaceutical composition according to embodiments 1-58, wherein the pharmaceutically-acceptable adjuvant is a liquid at 20° C.
60. The pharmaceutical composition according to embodiments 1-58, wherein the pharmaceutically-acceptable adjuvant is a solid at 20° C.
61. The pharmaceutical composition according to embodiments 1-60, wherein the pharmaceutically-acceptable adjuvant comprises a pharmaceutically-acceptable lipid.
62. The pharmaceutical composition according to embodiment 61, wherein the pharmaceutically-acceptable lipid comprises a saturated fatty acid, an unsaturated fatty acid, or a combination thereof.
63. The pharmaceutical composition according to embodiment 61 or 62, wherein the pharmaceutically-acceptable lipid comprises two or more saturated or unsaturated fatty acids.
64. The pharmaceutical composition according to embodiment 63, wherein the two or more saturated or unsaturated fatty acids includes palmitic acid, stearic acid, oleic acid, linoleic acid, linolenic acid, or a combination thereof.
65. The pharmaceutical composition according to embodiments 62-64, wherein the unsaturated fatty acid has a melting point temperature of 20° C. or below.
66. The pharmaceutical composition according to embodiments 62-64, wherein the unsaturated fatty acid is a solid at 20° C.
67. The pharmaceutical composition according to embodiments 62-64, wherein the unsaturated fatty acid comprises an omega fatty acid.
68. The pharmaceutical composition according to embodiment 61, wherein the pharmaceutically-acceptable lipid comprises a pharmaceutically-acceptable oil.
69. The pharmaceutical composition according to embodiment 68, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof.
70. The pharmaceutical composition according to embodiments 1-69, wherein the pharmaceutical composition further comprises a pharmaceutically-acceptable stabilizing agent.
71. The pharmaceutical composition according to embodiment 70, wherein the pharmaceutically-acceptable stabilizing agent comprises water, a sacrificial acid comprising a fatty acid component and acetic acid, ethyl acetate, a sodium acetate/acetic acid, a monoglyceride, an acetylated monoglyceride, a diglyceride, an acetylated diglyceride, a fatty acid, a fatty acid salt, or a combination thereof.
72. The pharmaceutical composition according to embodiment 70, wherein the pharmaceutically-acceptable stabilizing agent comprises a pharmaceutically-acceptable emulsifying agent.
73. The pharmaceutical composition according to embodiment 72, wherein the pharmaceutically-acceptable emulsifying agent comprises a surfactant, a polysaccharide, a lectin, a phospholipid, or a combination thereof.
74. The pharmaceutical composition according to embodiments 1-71, wherein the pharmaceutical composition does not comprise a pharmaceutically-acceptable emulsifying agent.
75. A method of preparing a pharmaceutical composition, the method comprising the step of contacting a therapeutic compound with a pharmaceutically-acceptable adjuvant under conditions which allow the formation of the pharmaceutical composition.
76. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition.
77. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-inflammatory activity, and b) contacting the solution formed in step (a) with a pharmaceutically-acceptable adjuvant under conditions which allow the formation of the pharmaceutical composition, wherein the ratio of the pharmaceutically-acceptable solvent to pharmaceutically-acceptable adjuvant is in a range from about 0:1 to about 1:25.
78. The method according to embodiments 75-77, wherein the therapeutic compound has a log P value indicating that the compound is soluble in an organic solvent.
79. The method according to embodiment 75-78, wherein the therapeutic compound has a log P value of more than 1.0.
80. The method according to embodiment 75-78, wherein the therapeutic compound has a log P value of more than 2.0.
81. The method according to embodiments 75-80, wherein the therapeutic compound has a polar surface area that is hydrophobic.
82. The method according to embodiments 75-81, wherein the therapeutic compound has a polar surface area that is less than 8.0 nm$^2$.
83. The method according to embodiments 75-81, wherein the therapeutic compound has a polar surface area that is less than 6.0 nm$^2$.
84. The method according to embodiments 75-83, wherein the therapeutic compound comprises a non-steroidal anti-inflammatory drug (NSAID).
85. The method according to embodiment 84, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a combination thereof.

86. The method according to embodiments 75-85, wherein the therapeutic compound comprises a PPARγ agonist.

87. The method according to embodiment 86, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.

88. The method according to embodiments 75-87, wherein the therapeutic compound comprises a nuclear receptor binding agent.

89. The method according to embodiment 88, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.

90. The method according to embodiments 75-89, wherein the therapeutic compound comprises an anti-hyperlipidemic agent.

91. The method according to embodiment 90, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.

92. The method according to embodiment 91, wherein the fibrate comprises Bezafibrate, Ciprofibrate, Clofibrate, Gemfibrozil, Fenofibrate, or a combination thereof.

93. The method according to embodiment 91, wherein the statin comprises Atorvastatin, Fluvastatin, Lovastatin, Pitavastatin, Pravastatin, Rosuvastatin, Simvastatin, or a combination thereof.

94. The method according to embodiment 91, wherein the niacin comprises acipimox, niacin, nicotinamide, vitamin B3, or a combination thereof.

95. The method according to embodiment 91, wherein the bile acid sequestrant comprises Cholestyramine, Colesevelam, Colestipol, or a combination thereof.

96. The method according to embodiment 91, wherein the cholesterol absorption inhibitor comprises Ezetimibe, a phytosterol, a sterol, a stanol, or a combination thereof.

97. The method according to embodiment 91, wherein the fat absorption inhibitor comprises Orlistat 98. The method according to embodiment 91, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.

99. The method according to embodiments 75-98, wherein the therapeutic compound comprises an ester of a therapeutic compound.

100. The method according to embodiments 75-99, wherein the therapeutic compound comprises an ester of a therapeutic compound according to embodiments 78-99.

101. The method according to embodiments 76-100, wherein the pharmaceutically-acceptable solvent is less than about 20% (v/v).

102. The method according to embodiments 76-101, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.

103. The method according to embodiments 76-102, wherein the pharmaceutically-acceptable solvent comprises a pharmaceutically-acceptable alcohol.

104. The method according to embodiment 103, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.

105. The method according to embodiment 103, wherein the pharmaceutically-acceptable alcohol comprises a $C_{1-20}$ alcohol.

106. The method according to embodiment 103, wherein the pharmaceutically-acceptable alcohol comprises methanol, ethanol, propanol, butanol, pentanol, 1-hexadecanol, or a combination thereof.

107. The method according to embodiment 103, wherein the pharmaceutically-acceptable solvent comprises a pharmaceutically-acceptable ester of pharmaceutically-acceptable alcohol and an acid.

108. The method according to embodiment 107, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.

109. The method according to embodiments 76-108, wherein the pharmaceutically-acceptable solvent is a pharmaceutically-acceptable polyethylene glycol (PEG) polymer.

110. The method according to embodiment 109, wherein the pharmaceutically-acceptable polyethylene glycol (PEG) polymer is less than about 2,000 g/mol.

111. The method according to embodiment 109, wherein the pharmaceutically-acceptable polyethylene glycol (PEG) polymer is more than about 2,000 g/mol.

112. The method according to embodiments 76-111, wherein the pharmaceutically-acceptable solvent comprises a pharmaceutically-acceptable glyceride.

113. The method according to embodiments 112, wherein the pharmaceutically-acceptable glyceride is a monoglyceride, a diglyceride, a triglyceride, an acetylated monoglyceride, an acetylated diglyceride, an acetylated triglyceride, or a combination thereof.

114. The method according to embodiments 76-113, wherein the pharmaceutically-acceptable solvent is a liquid at 20° C.

115. The method according to embodiments 76-113, wherein the pharmaceutically-acceptable solvent is a solid at 20° C.

116. The method according to embodiment 113, wherein the pharmaceutically-acceptable solid solvent is menthol.

117. The method according to embodiments 75-116, wherein the pharmaceutically-acceptable adjuvant is at least 80% (v/v).

118. The method according to embodiments 75-117, wherein the pharmaceutically-acceptable adjuvant is a liquid at 20° C.
119. The method according to embodiments 75-117, wherein the pharmaceutically-acceptable adjuvant is a solid at 20° C.
120. The method according to embodiments 75-119, wherein the pharmaceutically-acceptable adjuvant comprises a pharmaceutically-acceptable lipid.
121. The method according to embodiment 120, wherein the pharmaceutically-acceptable lipid comprises a pharmaceutically-acceptable saturated fatty acid, an unsaturated fatty acid, or a combination thereof.
122. The method according to embodiment 120 or 121, wherein the pharmaceutically-acceptable lipid comprises two or more pharmaceutically-acceptable saturated or unsaturated fatty acids.
123. The method according to embodiments 122, wherein the two or more pharmaceutically-acceptable saturated or unsaturated fatty acids include palmitic acid, stearic acid, oleic acid, linoleic acid, linolenic acid, or a combination thereof.
124. The method according to embodiments 121-123, wherein the pharmaceutically-acceptable unsaturated fatty acid has a melting point temperature of 20° C. or below.
125. The method according to embodiments 121-123, wherein the pharmaceutically-acceptable unsaturated fatty acid is a solid at 20° C.
126. The method according to embodiments 121-125, wherein the pharmaceutically-acceptable unsaturated fatty acid comprises an omega fatty acid.
127. The method according to embodiments 120-126, wherein the pharmaceutically-acceptable lipid comprises a pharmaceutically-acceptable oil.
128. The method according to embodiment 127, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof.
129. The method according to embodiments 76 or 78-128, wherein in step (b) the ratio of the pharmaceutically-acceptable solvent to pharmaceutically-acceptable adjuvant is in a range from about 0:1 to about 1:25.
130. The method according to embodiments 75-129, wherein the step (a) further comprising contacting a pharmaceutically-acceptable stabilizing agent with the pharmaceutically-acceptable solvent and the therapeutic compound.
131. The method according to embodiment 130, wherein the pharmaceutically-acceptable stabilizing agent comprises water, a sacrificial acid comprising a fatty acid component and acetic acid, ethyl acetate, a sodium acetate/acetic acid, a monoglyceride, an acetylated monoglyceride, a diglyceride, an acetylated diglyceride, a fatty acid, a fatty acid salt, or a combination thereof.
132. The method according to embodiment 130 or 131, wherein the pharmaceutically-acceptable stabilizing agent comprises a pharmaceutically-acceptable emulsifying agent.
133. The method according to embodiment 132, wherein the pharmaceutically-acceptable emulsifying agent comprises a surfactant, a polysaccharide, a lectin, a phospholipid, or a combination thereof.
134. The method according to embodiments 75-131, wherein the pharmaceutical composition does not comprise a pharmaceutically-acceptable emulsifying agent.
135. The method according to embodiments 76-134, wherein the method further comprises removing the pharmaceutically-acceptable solvent from the pharmaceutical composition.
136. The method according to embodiment 135, wherein at least 5% the pharmaceutically-acceptable solvent is removed from the pharmaceutical composition.
137. The method according to embodiment 135 or 136, wherein at, removal of solvent from the pharmaceutical composition disclosed herein is carried out at a temperature of less than 20° C.
138. The method according to embodiments 75-137, wherein the pharmaceutical composition made is according to embodiments 1-74.
139. A method of treating an individual with a cardiovascular disease, the method comprising the step of: administering to the individual in need thereof a pharmaceutical composition according to embodiments 1-74, wherein administration results in a reduction in a symptom associated with the cardiovascular disease, thereby treating the individual.
140. Use of a pharmaceutical composition according to embodiments 1-74 in the manufacture of a medicament for the treatment of a cardiovascular disease.
141. Use of a pharmaceutical composition according to embodiments 1-74 for the treatment of a cardiovascular disease.
142. The method according to embodiment 139 or the use according to embodiment 140 or 141, wherein the cardiovascular disease is associated with a hyperlipidemia, a coronary heart disease, an atherosclerosis, a peripheral vascular disease, a cardiomyopathy, a vasculitis, an inflammatory heart disease, an ischemic heart disease, a congestive heart failure, a hypertensive heart disease, a valvular heart disease, a hypertension, myocardial infarction, a diabetic cardiac conditions, an aneurysm; an embolism, a dissection, a pseudoaneurysm, a vascular malformation, a vascular nevus, a thrombosis, a varicose vein, or a stroke.
143. The method or use according to embodiment 142, wherein the hyperlipidemia is dyslipidemia, hypercholesterolemia, hyperglyceridemia, hypertriglyceridemia, hyperlipoproteinemia, or hyperchylomicronemia, and combined hyperlipidemia.
144. The method or use according to embodiment 143, wherein the hyperlipoproteinemia is hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, or hyperlipoproteinemia type V.
145. The method or use according to embodiment 142, wherein the vascular occlusive disease (VOD) is an atherosclerosis, a peripheral vascular disease, or a stenosis.
146. The method or use according to embodiment 142, wherein the cardiomyopathy is an extrinsic cardiomyopathy or an intrinsic cardiomyopathy.
147. The method or use according to embodiment 146, wherein the extrinsic cardiomyopathy is acromegaly, alcoholic cardiomyopathy, amyloidosis, Chagas disease, chemotherapy, diabetic cardiomyopathy, hemochromatosis, hypertensive cardiomyopathy, hyperthyroidism, inflammatory cardiomyopathy, ischemic cardiomyopathy, muscular dystrophy, valvular cardiomyopathy, a cardiomyopathy secondary to a systemic metabolic disease, a cardiomyopathy secondary to a systemic nutritional disease, a coronary artery disease, or a congenital heart disease.

148. The method or use according to embodiment 146, wherein the intrinsic cardiomyopathy is dilated cardiomyopathy (DCM), hypertrophic cardiomyopathy (HCM or HOCM), arrhythmogenic right ventricular cardiomyopathy (ARVC), restrictive cardiomyopathy (RCM), non-compaction cardiomyopathy, isolated ventricular non-compaction, mitochondrial myopathy, Takotsubo cardiomyopathy, or Loeffler endocarditis.

149. The method or use according to embodiment 142, wherein the vasculitis is a Buerger's disease, an arteritis, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a phlebitis, a microscopic polyarteritis/polyangiitis, a polyarteritis nodosa, a polymyalgia rheumatica (PMR), a rheumatoid vasculitis, a Takayasu arteritis, a thrombophlebitis, a Wegener's granulomatosis, or a vasculitis secondary to connective tissue disorder, or vasculitis secondary to viral infection.

150. The method or use according to embodiment 149, wherein the vasculitis secondary to connective tissue disorder is systemic lupus erythematosus (SLE), rheumatoid arthritis (RA), relapsing polychondritis, Behçet's disease.

151. The method or use according to embodiment 142, wherein the inflammatory heart disease is an endocarditis, an inflammatory cardiomegaly, or a myocarditis.

152. The method according to embodiments 139 or 142-151 or the use according to embodiments 140-151, wherein upon administration to an individual, the pharmaceutical composition comprising the therapeutic compound according to embodiments 1-74 results in a bio-distribution of the therapeutic compound different than a bio-distribution of the therapeutic compound included in the same pharmaceutical composition, except without the pharmaceutically-acceptable adjuvant.

153. The method according to embodiments 139 or 142-152 or the use according to embodiments 140-152, wherein upon administration to an individual, the amount of the therapeutic compound of the pharmaceutical composition according to embodiments 1-74 delivered to a macrophage is at least 5% of the total amount of the therapeutic compound contained in the administered pharmaceutical composition.

154. The method according to embodiments 139 or 142-153 or the use according to embodiments 140-153, wherein upon administration to an individual, the pharmaceutical composition according to embodiments 1-74 reduces intestinal irritation by at least 5% when compared to the pharmaceutical composition according to embodiments 1-74, except without the pharmaceutically-acceptable adjuvant.

155. The method according to embodiments 139 or 142-154 or the use according to embodiments 140-154, wherein upon administration to an individual, the pharmaceutical composition according to embodiments 1-74 reduces gastric irritation by at least 5% when compared to the pharmaceutical composition according to embodiments 1-74, except without the pharmaceutically-acceptable adjuvant.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, alcohols, lipids, pharmaceutical compositions, methods of preparing pharmaceutical compositions, or methods or uses of treating a chronic inflammation or disease associated with chronic inflammation.

Example 1

Liquid Formulations of Pharmaceutical Composition

This example illustrates how to make a pharmaceutical composition as disclosed herein as a liquid formulation.

Initially, 2,400 mg of ibuprofen was contacted directly with 2.0 mL of rapeseed oil in an attempt to dissolve a therapeutic compound directly into an adjuvant at a concentration of 1,200 mg/mL. However, ibuprofen remained insoluble in the oil and did not dissolve to substantially measurable degree. Ibuprofen remained insolubility even if the mixture was mixed by vortexing for 20 seconds, the contacting was done at 20° C. or 37° C., and/or the mixture was allowed to incubate for 24 hours at 20° C. or 37° C. The insolubility of ibuprofen in rapeseed oil was surprising given that ibuprofen has a log P value of 3.6; such a high log P value is indicative of a compound that would readily soluble in an adjuvant like oil.

Since, it was not possible to dissolve ibuprofen directly into oil, despite its high log P value, it was next tried to dissolve a therapeutic drug in a solvent to first create a solution comprising the compound. As a first step, experiments were conducted to the miscibility of a solvent in an adjuvant like oil in the absence of a therapeutic compound. In these experiments 0.5 mL ethanol was contacted with ten different volumes of rapeseed oil (Table 1). Each mixture was tested at 22° C. and at 37° C. in which the ethanol and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol and rapeseed oil form immiscible layers, or a homogeneous mixture. The results are summarized in Table 1. Mixtures comprising solvent:adjuvant ratios of 1:1, 1:2, 1:3, 1:4, 1:5, and 1:6 formed immiscible layers at either 22° C. or at 37° C., either immediately or after 24 hours of incubation, indicating that the ethanol and oil did not mix well at these ratios. However, in solvent:adjuvant ratios above 1:7 a homogeneous mixture was formed under all conditions tested.

TABLE 1

Liquid Formulations without Therapeutic compound

| Components | | | Temperature | | | |
| --- | --- | --- | --- | --- | --- | --- |
| | | | 22° C. | | 37° C. | |
| Solvent (mL) | Adjuvant (mL) | Ratio | Immediate | 24 hours | Immediate | 24 hours |
| 0.5 | 0.5 | 1:1 | IL | IL | IL | IL |
| 0.5 | 1.0 | 1:2 | IL | IL | IL | IL |

TABLE 1-continued

Liquid Formulations without Therapeutic compound

| Components | | | Temperature | | | |
|---|---|---|---|---|---|---|
| | | | 22° C. | | 37° C. | |
| Solvent (mL) | Adjuvant (mL) | Ratio | Immediate | 24 hours | Immediate | 24 hours |
| 0.5 | 1.5 | 1:3 | IL | IL | IL | IL |
| 0.5 | 2.0 | 1:4 | IL | IL | IL | IL |
| 0.5 | 2.5 | 1:5 | IL | IL | IL | IL |
| 0.5 | 3.0 | 1:6 | IL | IL | IL | IL |
| 0.5 | 3.5 | 1:7 | HM | HM | HM | HM |
| 0.5 | 4.0 | 1:8 | HM | HM | HM | HM |
| 0.5 | 4.5 | 1:9 | HM | HM | HM | HM |
| 0.5 | 5.0 | 1:10 | HM | HM | HM | HM |

IL, Immiscible layers.
HM, Homogeneous mixture.

Once the appropriate ratios of alcohol and lipid necessary to form a homogenous mixture were determined, it was next determined whether contacting a therapeutic compound first in a solvent before contacting with an adjuvant would result in the compound dissolving in the solvents. To conduct these experiments, either 1,000 mg or 1,200 mg of ibuprofen was dissolved into 0.5 mL of ethanol. The resulting alcohol solution was then contacted with rapeseed oil at two different solvent:adjuvant ratios (1:2 and 1:9). Each mixture was tested at 20° C. and at 37° C. in which the ethanol solution and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol solution and rapeseed oil form immiscible layers, or a homogeneous mixture. The results are summarized in Table 2. In contrast to the situation in the absence of a therapeutic compound, when ibuprofen is present in the ethanol, it caused the ethanol and oil to form a homogeneous mixture under all conditions tested in solvent:adjuvant ratios above 1:2. This observation was very surprising because, although not wish to be bound by any theory, it appears that a therapeutic compound may be having some effect on the manner in which an adjuvant and solvent interact with each other, such that a homogeneous mixture is formed in a way that does not occur when the therapeutic compound is absent. In addition, the results indicate that a therapeutic compound can be formulated at clinically useful concentrations.

TABLE 2

Liquid Formulations with Therapeutic Compound

| Components | | | | Temperature | | | |
|---|---|---|---|---|---|---|---|
| | | | | 22° C. | | 37° C. | |
| Compound (mg) | Solvent (mL) | Adjuvant (mL) | Ratio | Immediate | 24 hours | Immediate | 24 hours |
| 500 | 0.5 | 1.0 | 1:2 | HM | HM | HM | HM |
| 600 | 0.5 | 1.0 | 1:2 | HM | HM | HM | HM |
| 500 | 0.5 | 4.5 | 1:9 | HM | HM | HM | HM |
| 600 | 0.5 | 4.5 | 1:9 | HM | HM | HM | HM |

IL, Immiscible layers.
HM, Homogeneous mixture.

Example 2

Liquid Formulations of Pharmaceutical Composition

This example illustrates how to make a pharmaceutical composition as disclosed herein as a liquid formulation.

To prepare a pharmaceutical composition disclosed herein using gemfibrozil, the following formulations were examined. In these experiments, 600 mg gemfibrozil was contacted with different volumes of ethanol, as the solvent, warmed to 37° C., and the resulting solution was then contacted with different volumes of linseed oil, as the adjuvant, warmed to 37° C. (Table 3). Each formulation was evaluated to determine whether or not the ethanol and linseed oil form immiscible layers, a clear homogeneous mixture, as well as whether or not the gemfibrozil crystallized out of solution. The results are summarized in Table 3.

Like ibuprofen in Example 1 above, gemfibrozil remained insoluble in the oil alone and did not dissolve to substantially measurable degree. The formulation comprising 0.2 mL ethanol was unable to completely dissolve gemfibrozil. In addition, although the formulation comprising 0.3 mL ethanol was capable of dissolving gemfibrozil, the therapeutic compound began to crystallizing out of solution within 3 hours and complete crystallization occurred within 48 hours. All other formulations tested were capable of dissolving gemfibrozil and forming a pharmaceutical composition disclosed herein. However, only the formulation comprising 0.5 mL ethanol appeared to for a stable pharmaceutical composition in that gemfibrozil remained completely dissolved after three weeks.

TABLE 3

Liquid Formulations with Therapeutic Compound

| Components | | | | Temperature | |
|---|---|---|---|---|---|
| | | | | 22° C. | |
| Compound (mg) | Solvent (mL) | Adjuvant (mL) | Ratio | Immediate | 3 weeks |
| 600 | 0 | 1.0 | — | IM | N/A |
| 600 | 0.2 | — | — | IM | N/A |
| 600 | 0.3 | 0.6 | 1:2 | CR | CR |
| 600 | 0.4 | 0.4 | 1:1 | HM | CR |
| 600 | 0.4 | 0.8 | 1:2 | HM | CR |
| 600 | 0.5 | 1.0 | 1:2 | HM | HM |

HM, Clear homogeneous mixture.
CR, Crystallization.
IM, Immiscible.

Example 3

Liquid Formulations of Pharmaceutical Composition

This example illustrates how to make a pharmaceutical composition as disclosed herein as a liquid formulation.

To prepare a pharmaceutical composition disclosed herein using ibuprofen, the following formulation was performed. In these experiments, 4 g ibuprofen was contacted with 3.6 mL of ethyl acetate, as the solvent, and the resulting solution was then contacted with 76.4 mL of rapeseed oil, as the adjuvant. The resulting pharmaceutical composition had a solvent:adjuvant ratio of about 1:21. This pharmaceutical composition was then placed in a round bottom flask and subjected to low pressure on a rotary evaporator. The temperature was kept low and evaporation continued to constant weight. The total volume lost was 3.65% of the total weight. The resulting liquid no longer retained the characteristic ethyl acetate odor/taste, indicating that there was a substantial removal of ethyl acetate form the pharmaceutical composition.

Example 4

Solid Formulation of Pharmaceutical Composition

This example illustrates how to make a pharmaceutical composition as disclosed herein as a solid formulation.

Since certain fatty acids are liquid at room temperature, while others are solid, an examination of the different fatty acids was undertaken in an effort to evaluate the potential of each fatty acid in the manufacture of a solid formulation. This understanding would enable the development of a wide array of solid formulation by adjusting the relative ratios of each fatty acid. As an initial experiment, linolenic acid, linoleic acid, palmitic acid and stearic acid were evaluated to assess whether it was possible to prepare a pharmaceutical composition disclosed herein that could be formulated using only one of these fatty acids to be a solid or semi-solid at 22° C. (simulating room temperature conditions), but melt into a liquid at 37° C. (simulating internal body temperature conditions after ingestion).

Four different test formulations were prepared and evaluated on their ability to form a solid dose formulation at 22° C. and melt into a homogeneous solution at 37° C. without forming a suspension (Table 4). Formulation 1 was prepared by dissolving 200 mg of Ibuprofen into 400 mg of menthol, and the resulting solution was then mixed with 200 mg of stearic acid ($T_m$ of about 67-72° C.) and heated at 60° C. for 30 minutes to form a homogeneous solution. Formulation 1 solidified immediately upon cooling to 22° C. Formulation 1 remained a solid even after incubating at 37° C. overnight. Formulation 2 was prepared by dissolving 200 mg of Ibuprofen into 400 mg of menthol, and the resulting solution was then mixed with 200 mg of palmitic acid ($T_m$ of about 61-62° C.) and heated at 60° C. for 30 minutes to form a homogeneous solution. Formulation 2 solidified about 1 hour after cooling to 22° C. Incubating at 37° C. overnight cause Formulation 2 to completely melt into a clear homogenous liquid. However, Formulation 2 once again solidified about 1 hour after cooling to 22° C. Formulation 3 was prepared by dissolving 200 mg of Ibuprofen into 400 mg of menthol, and the resulting solution was then mixed with 200 mg of linoleic acid ($T_m$ of about −5° C.) and heated at 37° C. for 2 hours to form a homogeneous solution. Formulation 3 remained a liquid, even after cooling to 22° C. for 72 hours. Formulation 4 was prepared by dissolving 200 mg of Ibuprofen into 400 mg of menthol, and the resulting solution was then mixed with 200 mg of linolenic acid ($T_m$ of about −11° C.) and heated at 37° C. for 2 hours to form a homogeneous solution. Formulation 4 remained a liquid, even after cooling to 22° C. for 72 hours.

TABLE 4

Solid Formulations with Therapeutic Compound

| Components | | | | Temperature | | |
|---|---|---|---|---|---|---|
| Compound | Solvent | Adjuvant | | 22° C. | 37° C. | |
| (mg) | (mg) | (mg) | Ratio | Upon Cooling | 24 hours | 72 hours |
| 200 | 400 | 200 (stearic acid) | 2:1 | Solid | Solid | — |
| 200 | 400 | 200 (palmitic acid) | 2:1 | Solid | Liquid | — |
| 200 | 400 | 200 (linoleic acid) | 2:1 | Liquid | Liquid | Liquid |
| 200 | 400 | 200 (linolenic acid) | 2:1 | Liquid | Liquid | Liquid |

Based on these data, a solid dosage form of a pharmaceutical composition disclosed herein can be made. For example, a pharmaceutical composition will be formulated to be solid or semi-solid at 22° C., but melt into a proper clear solution (and not a suspension) at 37° C. (Table 5).

TABLE 5

Solid Formulations of Pharmaceutical Compositions

| | |
|---|---|
| Compound | 600 mg Ibuprofen |
| Solvent | 500 mg Methanol |
| Adjuvant | 2000 mg Palmitic acid |
| | 2000 mg Stearic acid |
| | 250 mg Linolenic acid |
| | 250 mg Linoleic acid |
| Ratio | 1:9 |
| Volume | 5 mL |
| Concentration | 120 mg/mL |

Example 5

Animal Model for Intestinal Erosion

To assess whether a pharmaceutical composition disclosed herein reduced gastric irritation, experiments were conducted using an intestinal erosion murine model.

Sprague-Dawley rats were divided into seven experimental groups containing five animals each. After fasting overnight, the animals were challenged with one with one of seven different treatments. Group A was a control in which each mouse was orally administered 1% methylcellulose/0.5% polysorbate 80 vehicle only. Group B was a control in which each mouse was orally administered solvent/adjuvant vehicle only (gavage of 10% ethanol and 90% linseed oil). Group C was a control in which each mouse was orally administered 150 mg/kg aspirin. Group D was a control in which each mouse was orally administered 100 mg/kg ibuprofen suspended in 1% methylcellulose/0.5% polysorbate 80. Group E was the experimental group in which each mouse was administered a pharmaceutical composition disclosed herein (BC1054-100) comprising 100 mg/kg of ibuprofen, 10% ethanol, and 90% linseed oil. Group F was a control in which each mouse was orally administered 100 mg/kg ibuprofen suspended in 1% methylcellulose/0.5% polysorbate 80. Group G was the experimental group in which each mouse was administered a pharmaceutical composition disclosed herein (BC1054-200) comprising 200 mg/kg of ibuprofen, 10% ethanol, and 90% linseed oil. Animals were sacrificed 4 hours after treatment and the stomachs were examined for degree of hemorrhage and severity of mucosal erosive lesions. Gastric irritation was scored as follows: 0, no lesions; 1, hyperemia; 2, one or two slight lesions; 3, more than two slight lesions or severe lesions; and 4, very severe lesions. A score of 50% or more relative to Group C (aspirin-treated control group), which was set to 100%, was considered a positive score for gastric irritation.

Results are shown in Table 6. Group D (100 mg/kg of ibuprofen-treated control group) and Group F (200 mg/kg of ibuprofen-treated control group) produced gastric lesions that were 75% and 95%, respectively, severe as those induced by Group C (aspirin-treated control group). However, Group E (BC1054-100-treated experimental group) and Group G (BC1054-200-treated experimental group) produced gastric lesions that were 20% and 40%, respectively, as severe as those associated with Group C (aspirin-treated control group). These results demonstrate that that a pharmaceutical composition disclosed herein reduced the extent to which a therapeutic compound may cause mucosal lesions and cause gastric irritation.

TABLE 6

Results from Intestinal Erosion Assay

| Group | Mean Ulceration Score | % Aspirin Erosion |
|---|---|---|
| A | 0 | 0 |
| B | 0 | 0 |
| C | 4 | (100) |
| D | 3 | 75[1] |
| E | 0.8 | 20 |
| F | 3.8 | 95[1] |
| G | 1.6 | 40 |

[1]Positive score for gastric erosion.

Example 6

Animal Model for a Respiratory Inflammation

To assess the effectiveness of a pharmaceutical composition disclosed herein in treating a respiratory inflammation, experiments were conducted using a viral-induce influenza murine model.

C57BLK/6 female mice (6-7 weeks old) were divided into three experimental groups containing ten animals each. On day 1, animals received an intranasal lethal dose (50 µL total, 25 µL/nostril) of Influenza A/PR/8/34 under halothane-induced anaesthesia. On day 3, post-challenge with the virus, the animals received one of three treatments. Group A was a control in which each mouse was orally administered 335.6 µg of ibuprofen dissolved in 10 µL DMSO (no adjuvant). Group B was a control in which each mouse was orally administered solvent/adjuvant vehicle only (gavage of 10% ethanol and 90% linseed oil). Group C was the experimental group in which each mouse was administered a pharmaceutical composition disclosed herein (BC1054) comprising 335.6 µg of ibuprofen, 10% ethanol, and 90% linseed oil. A dose of 335.6 µg of ibuprofen in the mouse is equivalent to 20 mg/kg/day, or 1200 mg/day for a human (the maximum standard dose for ibuprofen). Animals were weighed, and monitored for signs of infection daily for up to day 6 when all animals were culled. FIG. 1 clearly shows that oral administration of the solvent/adjuvant vehicle only (Group B) had an 80% mortality rate and that oral administration of ibuprofen only (Group A) exhibited a mortality rate of 60%. However, a single oral administration of BC1054 reduced the mortality rate to only 20%.

To determination of levels of IL-10 and IL-4, an ELISA was performed using a 96-well plate coated with a capture antibody for IL-10 or IL-4. Lungs collected from the culled mice were homogenized at 4° C., and the supernatant collected and stored at −70° C. until needed. Thawed samples were vortexed for 30 seconds immediately before adding to the ELISA plate. Serial dilutions were performed within the plate with both the sample and the standards by pipetting 60 µL of assay diluent into each well. The plate was sealed and incubated for 2 hours at room temperature. For IL-4, 60 µL of working detector was added (Detection Antibody+SAv-HRP reagent) to each well. The plate was sealed and incubated for 1 hour at room temperature. For IL-10, 60 µL of detection antibody was diluted in assay diluent to each well. Plates were washed and 60 µL of SAv-HRP enzyme was diluted in assay diluent and added to the plate. The plate was sealed and incubated for 20 minutes at room temperature. Plates were then washed ten times. 60 µL of substrate solution were added to each well and the plate was incubated for 30 minutes at room temperature in the dark. 60 µL of stop solution was added to each well and absorbance was read at 450 nm. IL-10 and IL-4 concentrations were expressed as pg/mg of lung tissue. These results indicate that a pharmaceutical composition disclosed herein was effective in treating a respiratory inflammation.

Figure 2A:
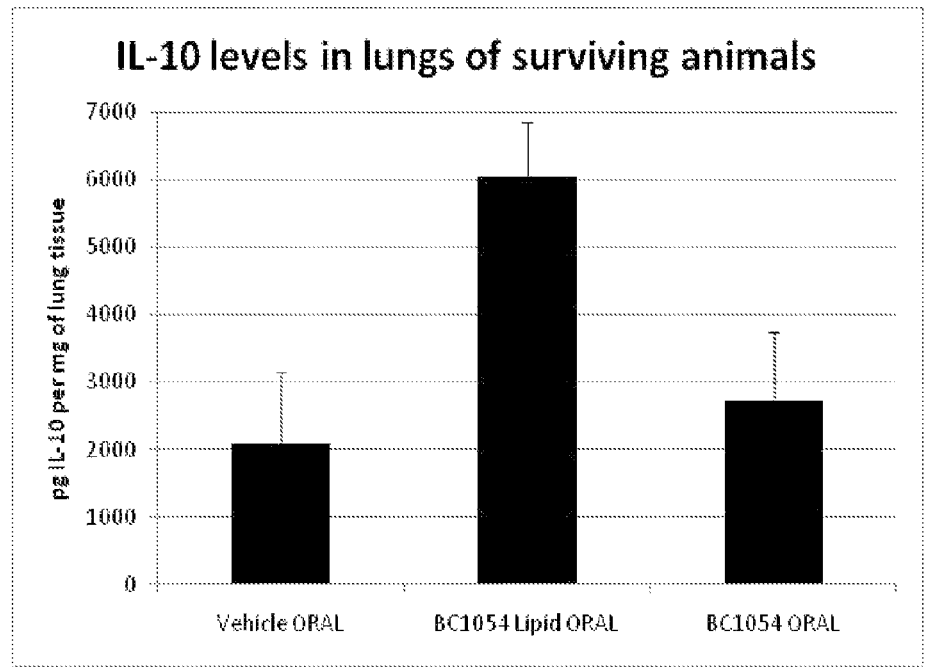
FIGS. 2A-B show the effects of a pharmaceutical composition disclosed herein on in vivo levels of Th2 cytokines in the lungs of surviving mice.
Figure 2B:
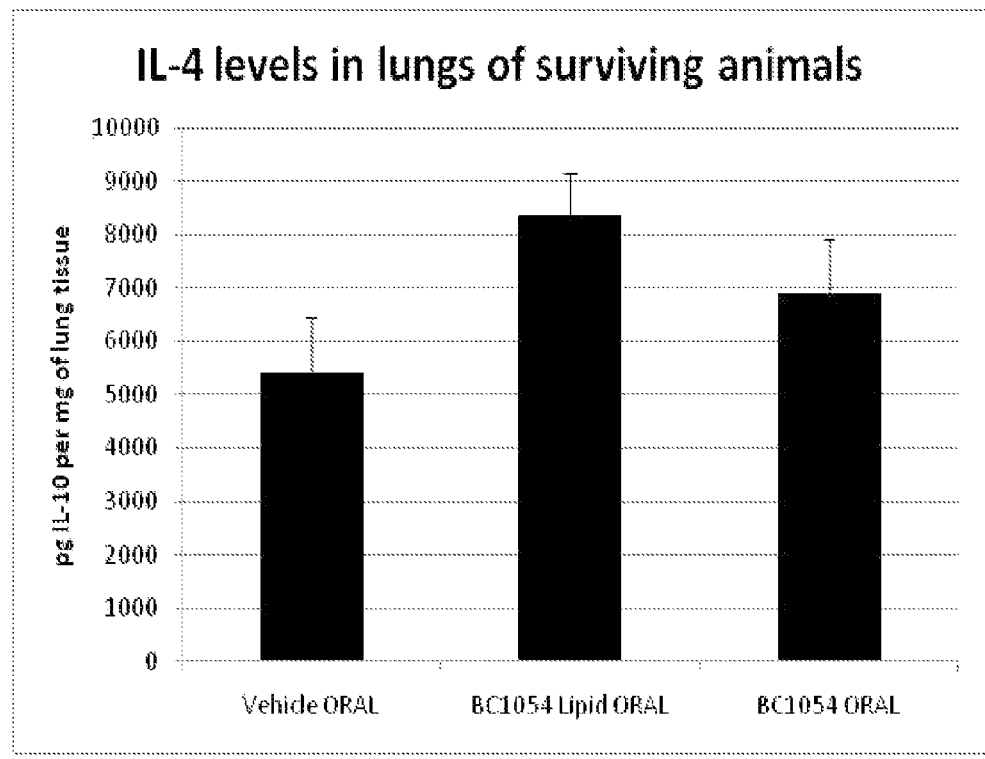

Results show that animals from the Group A (ibuprofen-treated control group) and Group B (solvent/adjuvant vehicle-treated control group) controls exhibited 2600 pg/mg and 2000 pg/mg of IL-10, respectively (FIG. 2A). However, Group C (BC1054-treated experimental group) revealed an IL-10 concentration of 6000 pg/mg, 3-fold higher than that seen in the control animals. These result also shows that animals from the Group A (ibuprofen-treated control group) and Group B (solvent/adjuvant vehicle-treated control group) controls exhibited 6900 pg/mg and 5400 pg/mg of IL-4, respectively, while Group C (BC1054-treated experimental group) exhibited an IL-4 concentration of 8300 pg/mg (FIG. 2B). Taken together, synergistic increase in IL-10 levels and/or the increase in IL-4 levels suggest that at least part of the efficacy observed for BC1054 was by inducing a switch from a Th1 to a Th2 response.

Further experiments were done to further determine which cell types were stimulated to release cytokines upon administration of a BC1054. C57BLK/6 female mice (6-7 weeks old) were divided into three experimental groups containing ten animals each. On day 1, animals received an intranasal lethal dose (50 µL total, 25 µL/nostril) of Influenza H1N1 under halothane-induced anaesthesia. On day 3, post-challenge with the virus, the animals received one of three treatments. Group A was a control in which each mouse was orally administered 335.6 µg of ibuprofen dissolved in 10 µL DMSO (no adjuvant). Group B was a control in which each mouse was orally administered solvent/adjuvant vehicle only (gavage of 10% ethanol and 90% linseed oil) (no ibuprofen). Group C was the experimental group in which each mouse was administered a pharmaceutical composition disclosed herein (BC1054) comprising 335.6 µg of ibuprofen, 10% ethanol, and 90% linseed oil. Lungs collected from fatally-infected mice were homogenized at 4° C., and the supernatant collected, stored, and IL-10, TNFα and IFNγ levels measured using an ELISA.

Figure 3A:
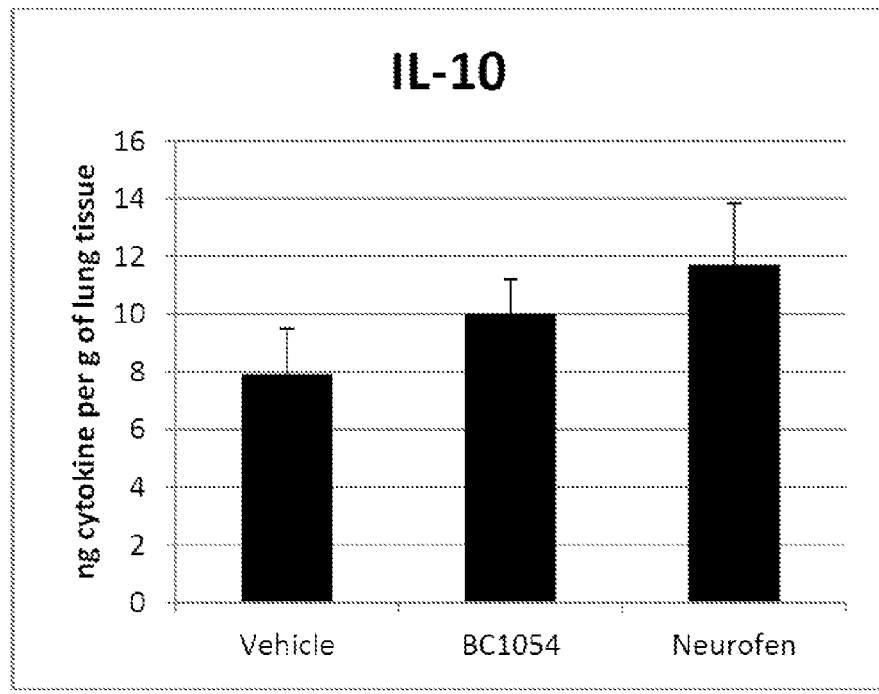
FIGS. 3A-C show the effects of a pharmaceutical composition disclosed herein on in vivo levels of Th2 cytokines in the lungs of surviving mice.
Figure 3B:
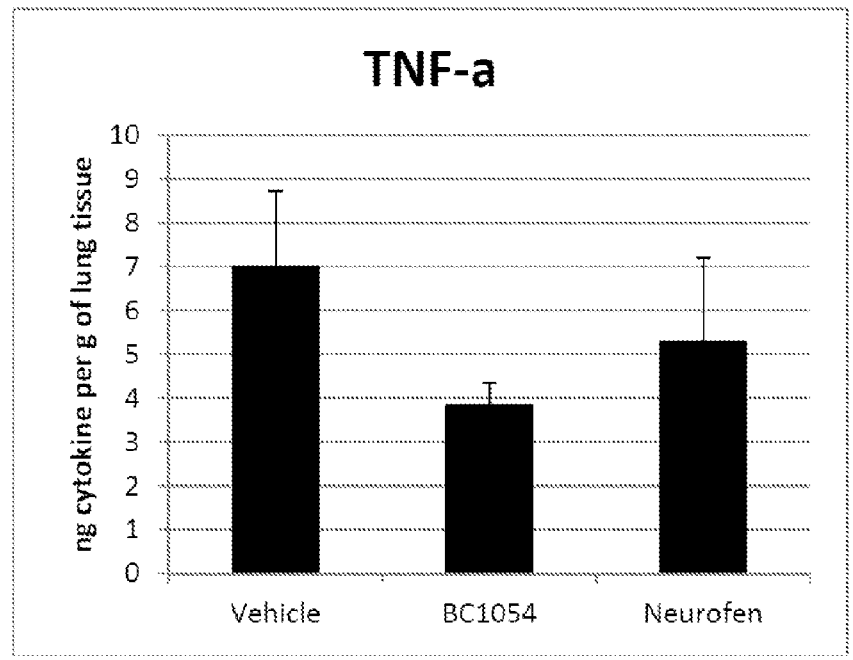
Figure 3C:
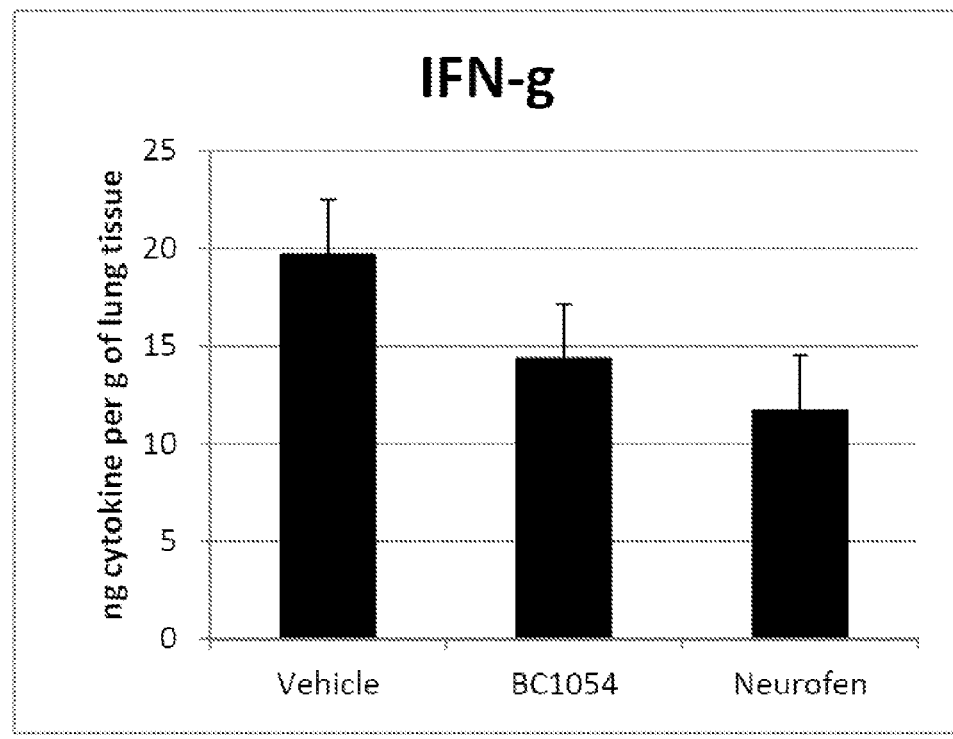

The results show that Group A (ibuprofen-treated control group) and Group C (BC1054-treated experimental group) animals exhibited an increased IL-10 levels (FIG. 3A). However, these IL-10 increases were associated with very different pharmacodynamic effects, and the pattern of pro-inflammatory cytokine reduction highlights the source of the IL-10 and its relevance to the effect on survival. For example, TNFα (which is macrophage-related cytokine) was not as markedly inhibited (FIG. 3B) in Group A (ibuprofen-treated control group) animals, whereas the levels of IFNγ (which is a lymphocyte-derived cytokine) were markedly lowered in this group when compared to Group C (BC1054-treated experimental group) animals (FIG. 3C). This cytokine release pattern was associated with a poor outcome. However, in Group C (BC1054-treated experimental group) animals, TNFα levels were markedly lowered (FIG. 3B), while IFNγ levels were largely unaffected (FIG. 3C). This demonstrates that a pharmaceutical composition disclosed herein shows a protective effect on the H1N1-induced lethality through, in part, a macrophage-derived IL-10 levels rather than lymphocyte-derived IL10.

Example 7

Case Studies for the Treatment of a Cardiovascular Disease

A 49 year old male diagnosed with hypercholesterolemia (LDL of 4.35 mmol/L) was placed on a pharmaceutical composition disclosed herein (BC1054) comprising 20 mg/kg of ibuprofen, 10% ethanol, and 90% linseed oil (600 mg bid) for 7 days. After 5 days of treatment the patient's LDL levels had normalized to 3.89 mmol/L. The normalization of LDL level persisted for 2 months after cessation of BC1054 dosing, as determined at the last examination.

A 60 year old male newly diagnosed with hypercholesterolemia (LDL of 4.31 mmol/L) was given a course of a pharmaceutical composition disclosed herein (BC1054) comprising 20 mg/kg of ibuprofen, 10% ethanol, and 90% linseed oil (1200 mg uid) to lower LDL levels to within the normal range. After 5 days of treatment the patients LDL levels were lowered to 3.36 mmol/L. The patient was followed up for 1 month and his LDL remained within the normal range, despite there being no further BC1054 dosing.

Example 8

Treatment of Cardiovascular Disease

A 62 year old female is diagnosed with elevated cholesterol levels. A physician determines that the elevated cholesterol level is due to a hypercholesterolemia. The woman is treated by oral administration a pharmaceutical composition comprising ibuprofen as disclosed herein taken twice daily. Alternatively, the woman is treated by oral administration a pharmaceutical composition comprising a PPAR-γ agonist as disclosed herein taken thrice daily. Alternatively, the woman is treated by oral administration a pharmaceutical composition comprising Gemfibrozil as disclosed herein taken twice daily. The woman's condition is monitored and after about 1 week of treatment tests indicates there is reduced level of cholesterol in her blood. At one and three month check-ups, the woman continues to have blood cholesterol levels in a normal range. This reduction in a hypercholesterolemia symptom indicates successful treatment with the pharmaceutical composition disclosed herein. A similar type of oral administration of a pharmaceutical composition disclosed herein will be used to treat a patient suffering from other forms of, such as, e.g., dyslipidemia, hypercholesterolemia, hyperglyceridemia, hypertriglyceridemia, hyperchylomicronemia, combined hyperlipidemia, or hyperlipoproteinemia including hyperlipoproteinemia is hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, and hyperlipoproteinemia type V. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

A 58 year old male is complains of chest pains, shortness of breath and dizziness. A physician determines that the breathing difficulty is due to an atherosclerosis. The man is treated by oral administration a pharmaceutical composition comprising ibuprofen as disclosed herein taken twice daily. Alternatively, the man is treated by oral administration a pharmaceutical composition comprising a PPAR-γ agonist as disclosed herein taken thrice daily. Alternatively, the man is treated by oral administration a pharmaceutical composition comprising Gemfibrozil as disclosed herein taken twice daily. The man's condition is monitored and after about 3 weeks of treatment the man indicates there is improvement in his ability to breath and he is not experiencing as much dizziness. At two and three month check-ups, the man indicates that he continues to have improved breathing, no dizziness and no recent chest pains. This reduction in a atherosclerosis symptoms indicate successful treatment with the pharmaceutical composition disclosed herein. A similar type of oral administration of a pharmaceutical composition disclosed herein will be used to treat a patient suffering from another form of vascular occlusive disease such as, e.g., a peripheral vascular disease or a stenosis. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

A 67 year old male suffering from alcoholism complains of pressure on his chest and numbness in his left shoulder.

A physician determines that the pressure and numbness are due to an alcoholic cardiomyopathy. The man is treated by oral administration a pharmaceutical composition comprising ibuprofen as disclosed herein taken twice daily. Alternatively, the man is treated by oral administration a pharmaceutical composition comprising a PPAR-γ agonist as disclosed herein taken thrice daily. Alternatively, the man is treated by oral administration a pharmaceutical composition comprising Gemfibrozil as disclosed herein taken twice daily. The man's condition is monitored and after about 3 weeks of treatment the man indicates there is reduced numbness. At two and three month check-ups, the man indicates that he continues to have improved sensation in his shoulder and has not had a recent episode of chest pressure. This reduction in alcoholic cardiomyopathy symptoms indicates successful treatment with the pharmaceutical composition disclosed herein. A similar type of oral administration of a pharmaceutical composition disclosed herein will be used to treat a patient suffering from a cardiomyopathy, such as, e.g., an extrinsic cardiomyopathy like acromegaly, amyloidosis, Chagas disease, chemotherapy, diabetic cardiomyopathy, hemochromatosis, hypertensive cardiomyopathy, hyperthyroidism, inflammatory cardiomyopathy, ischemic cardiomyopathy, muscular dystrophy, valvular cardiomyopathy, a cardiomyopathy secondary to a systemic metabolic disease, a cardiomyopathy secondary to a systemic nutritional disease, a coronary artery disease, or a congenital heart disease; or an intrinsic cardiomyopathy like dilated cardiomyopathy (DCM), hypertrophic cardiomyopathy (HCM or HOCM), arrhythmogenic right ventricular cardiomyopathy (ARVC), restrictive cardiomyopathy (RCM), noncompaction cardiomyopathy, isolated ventricular noncompaction, mitochondrial myopathy, Takotsubo cardiomyopathy, or Loeffler endocarditis. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

A 73 year old female complains of muscle cramping and cold sensation down her right leg. A physician determines that the symptoms are due to arteritis of the femoral artery. The woman is treated by oral administration a pharmaceutical composition comprising ibuprofen as disclosed herein taken twice daily. Alternatively, the woman is treated by oral administration a pharmaceutical composition comprising a PPAR-γ agonist as disclosed herein taken thrice daily. Alternatively, the woman is treated by oral administration a pharmaceutical composition comprising Gemfibrozil as disclosed herein taken twice daily. The woman's condition is monitored and after about 3 weeks of treatment the woman indicates that she has reduced muscle cramping and no cold sensations on her leg. At two and three month check-ups, the woman indicates that she still does not have muscle cramping or cold sensations. This reduction in arteritis symptoms indicates successful treatment with the pharmaceutical composition disclosed herein. A similar type of oral administration of a pharmaceutical composition disclosed herein will be used to treat a patient suffering from another type of vasculitis, such as, e.g., a Buerger's disease, an arteritis, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a phlebitis, a microscopic polyarteritis/polyangiitis, a polyarteritis nodosa, a polymyalgia rheumatica (PMR), a rheumatoid vasculitis, a Takayasu arteritis, a thrombophlebitis, a Wegener's granulomatosis, a vasculitis secondary to viral infection, or a vasculitis secondary to connective tissue disorder including systemic lupus erythematosus (SLE), rheumatoid arthritis (RA), relapsing polychondritis, or Behçet's disease. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

A 37 year old male complains of chest pains. A physician determines that the pain is due to an endocarditis. The man is treated by oral administration a pharmaceutical composition comprising ibuprofen as disclosed herein taken twice daily. Alternatively, the man is treated by oral administration a pharmaceutical composition comprising a PPAR-γ agonist as disclosed herein taken thrice daily. Alternatively, the man is treated by oral administration a pharmaceutical composition comprising Gemfibrozil as disclosed herein taken twice daily. The man's condition is monitored and after about 1 week of treatment the man indicates there is reduced chest pain. At one and three month check-ups, the man indicates that he continues to have no chest pain. This reduction in a endocarditis symptom indicates successful treatment with the pharmaceutical composition disclosed herein. A similar type of oral administration of a pharmaceutical composition disclosed herein will be used to treat a patient suffering from another type of inflammatory heart disease, such as, e.g., an inflammatory cardiomegaly or a myocarditis. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

A 59 year old female complains about having a shortness of breath and is diagnosed with high blood pressure. A physician determines that the joint stiffness and swelling is due to a hypertensive disease. The woman is treated by oral administration a pharmaceutical composition comprising ibuprofen as disclosed herein taken twice daily. Alternatively, the woman is treated by oral administration a pharmaceutical composition comprising a PPAR-γ agonist as disclosed herein taken thrice daily. Alternatively, the woman is treated by oral administration a pharmaceutical composition comprising Gemfibrozil as disclosed herein taken twice daily. The woman's condition is monitored and after about 3 weeks of treatment the woman indicates that her breathing is improving and her blood pressure is within the normal range. At two and three month check-ups, the woman indicates that she continues to breathe normally and her blood pressure is within the normal range. This reduction in a hypertensive symptom indicates successful treatment with the pharmaceutical composition disclosed herein. A similar type of oral administration of a pharmaceutical composition disclosed herein will be used to treat a patient suffering from a cardiovascular disease, such as, e.g., a coronary heart disease, an ischemic heart disease, a congestive heart failure, a hypertensive heart disease, a valvular heart disease, a hypertension, myocardial infarction, a diabetic cardiac conditions, an aneurysm; an embolism, a dissection, a pseudoaneurysm, a vascular malformation, a vascular nevus, a thrombosis, a varicose vein, or a stroke. In a similar manner, any of the therapeutic compounds such as, e.g., a NSAID like a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase 1 (COX 1) inhibitor, a selective cyclooxygenase 2 (COX 2) inhibitor; a PPARγ agonist; a nuclear receptor binding agent; or an anti-hyperlipidemic agent like a fibrate, a statin, a tocotrienol, a niacin, a bile acid sequestrants, a cholesterol absorption inhibitor, a pancreatic lipase inhibitor, or a sympathomimetic amine, will be formulated into a pharmaceutical composition and administered to the patient as described above.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A pharmaceutical composition comprising:
   a) an anti-hyperlipidemic agent having a log P value of more than 2.6; and
   b) at least 80% (v/v) of a pharmaceutically-acceptable lipid-adjuvant, wherein the pharmaceutically-acceptable lipid-adjuvant is a fatty acid having at least 12 carbons, a glycerolipid, a sterol lipid, a prenol lipid, a saccharolipid, or a polyketide,
   wherein the pharmaceutical composition is formulated to be a solid at 15° C. or lower and have a melting point temperature of about 30° C. or higher.

2. The pharmaceutical composition according to claim 1, wherein the anti-hyperlipidemic agent has a log P value of more than 2.8.

3. The pharmaceutical composition according to claim 1, wherein the anti-hyperlipidemic agent comprises a fibrate or a statin.

4. The pharmaceutical composition according to claim 3, wherein the fibrate comprises Bezafibrate, Ciprofibrate, Clofibrate, Gemfibrozil, Fenofibrate, or a combination thereof.

5. The pharmaceutical composition according to claim 3, wherein the statin comprises Atorvastatin, Fluvastatin, Lovastatin, Pitavastatin, Pravastatin, Rosuvastatin, Simvastatin, or a combination thereof.

6. The pharmaceutical composition according to claim 1, wherein the concentration of the fibrate or the statin is at least 50 mg/mL.

7. The pharmaceutical composition according to claim 1, wherein the pharmaceutically-acceptable lipid-adjuvant comprises a saturated fatty acid, an unsaturated fatty acid, or any combination thereof.

8. The pharmaceutical composition according to claim 1, wherein the pharmaceutically-acceptable lipid-adjuvant comprises a monoglyceride, an acetylated monoglyceride, a diglyceride, an acetylated diglyceride, a triglyceride, an acetylated triglyceride, or any combination thereof.

9. The pharmaceutical composition according to claim 8, wherein the pharmaceutically-acceptable lipid-adjuvant comprises a triglyceride, an acetylated triglyceride, or any combination thereof.

10. The pharmaceutical composition according to claim 1, wherein the pharmaceutically-acceptable lipid-adjuvant is in an amount of about 80% (v/v) to about 97% (v/v).

11. The pharmaceutical composition according to claim 1, wherein the pharmaceutically-acceptable lipid-adjuvant is in an amount of about 80% (v/v) to about 93% (v/v).

12. The pharmaceutical composition according to claim 11, wherein the pharmaceutically-acceptable lipid-adjuvant is in an amount of about 85% (v/v) to about 93% (v/v).

13. The pharmaceutical composition according to claim 12, wherein the pharmaceutically-acceptable lipid-adjuvant is in an amount of about 88% (v/v) to about 93% (v/v).

14. The pharmaceutical composition according to claim 13, wherein the pharmaceutically-acceptable lipid-adjuvant is in an amount of about 80% (v/v) to about 97% (v/v).

15. The pharmaceutical composition according to claim 14, further comprising a pharmaceutically-acceptable stabilizing agent.

16. A pharmaceutical composition comprising:
   a) a fibrate and/or a statin; and
   b) at least 80% (v/v) of a pharmaceutically-acceptable glycerolipid,
   wherein the pharmaceutical composition is formulated to be a solid at a temperature of 15° C. or lower and have a melting point temperature of about 30° C. or higher.

17. The pharmaceutical composition according to claim 16, wherein the fibrate comprises Bezafibrate, Ciprofibrate, Clofibrate, Gemfibrozil, Fenofibrate, or a combination thereof.

18. The pharmaceutical composition according to claim 16, wherein the statin comprises Atorvastatin, Fluvastatin, Lovastatin, Pitavastatin, Pravastatin, Rosuvastatin, Simvastatin, or a combination thereof.

19. The pharmaceutical composition according to claim 16, wherein the pharmaceutically-acceptable lipid-adjuvant comprises a monoglyceride, an acetylated monoglyceride, a diglyceride, an acetylated diglyceride, a triglyceride, an acetylated triglyceride, or any combination thereof.

20. The pharmaceutical composition according to claim 19, wherein the pharmaceutically-acceptable lipid-adjuvant comprises a triglyceride, an acetylated triglyceride, or any combination thereof.

* * * * *